(12) United States Patent
Kueny et al.

(10) Patent No.: US 10,365,212 B2
(45) Date of Patent: Jul. 30, 2019

(54) SYSTEM AND METHOD FOR CALIBRATION OF OPTICAL SIGNALS IN SEMICONDUCTOR PROCESS SYSTEMS

(71) Applicant: Verity Instruments, Inc., Carrollton, TX (US)

(72) Inventors: Andrew Weeks Kueny, Carrollton, TX (US); Mike Whelan, Carrollton, TX (US); Mark Anthony Meloni, Carrollton, TX (US); John D. Corless, Carrollton, TX (US); Rick Daignault, Carrollton, TX (US); Sean Lynes, Carrollton, TX (US)

(73) Assignee: Verity Instruments, Inc., Carrollton, TX (US)

( * ) Notice: Subject to any disclaimer, the term of this patent is extended or adjusted under 35 U.S.C. 154(b) by 0 days.

(21) Appl. No.: 15/802,286

(22) Filed: Nov. 2, 2017

(65) Prior Publication Data

US 2018/0136118 A1    May 17, 2018

Related U.S. Application Data

(60) Provisional application No. 62/456,424, filed on Feb. 8, 2017, provisional application No. 62/421,862, filed on Nov. 14, 2016.

(51) Int. Cl.

| | | |
|---|---|---|
| *H01J 1/00* | (2006.01) | |
| *G01N 21/27* | (2006.01) | |
| *G01J 3/28* | (2006.01) | |
| *G01J 3/443* | (2006.01) | |
| *G01N 21/66* | (2006.01) | |
| *H01J 37/32* | (2006.01) | |
| *H01L 21/68* | (2006.01) | |

(Continued)

(52) U.S. Cl.
CPC .......... *G01N 21/274* (2013.01); *G01J 3/2823* (2013.01); *G01J 3/443* (2013.01); *G01N 21/66* (2013.01); *G01N 21/73* (2013.01); *H01J 37/32963* (2013.01); *H01J 37/32972* (2013.01); *H01L 21/681* (2013.01); *H01L 22/26* (2013.01); *H05H 1/0006* (2013.01); *G01N 2021/8416* (2013.01); *H01J 2237/2482* (2013.01)

(58) Field of Classification Search
CPC .. H04N 5/33; G01J 5/522; G01T 1/40; G01D 18/00; A61B 6/583
See application file for complete search history.

(56) References Cited

U.S. PATENT DOCUMENTS

| | | |
|---|---|---|
| 4,676,594 A | 6/1987 | Presby |
| 5,571,366 A | 11/1996 | Ishii et al. |

(Continued)

*Primary Examiner* — David P Porta
*Assistant Examiner* — Mamadou Faye

(57) ABSTRACT

The disclosure provides an optical calibration device for in-chamber calibration of optical signals associated with a processing chamber, a characterization system for plasma processing chambers, methods of characterizing plasma processing chambers, and a chamber characterizer. In one example, the optical calibration device includes: (1) an enclosure, (2) an optical source located within the enclosure and configured to provide a source light having a continuous spectrum, and (3) optical shaping elements located within the enclosure and configured to form the source light into a calibrating light that approximates a plasma emission during an operation within the processing chamber.

27 Claims, 11 Drawing Sheets

(51) Int. Cl.
*H01L 21/66* (2006.01)
*H05H 1/00* (2006.01)
*G01N 21/73* (2006.01)
*G01N 21/84* (2006.01)

(56) References Cited

U.S. PATENT DOCUMENTS

| | | | |
|---|---|---|---|
| 6,633,391 B1 * | 10/2003 | Oluseyi | G01N 21/71 356/630 |
| 8,125,633 B2 | 2/2012 | Whelan et al. | |
| 2012/0326054 A1 * | 12/2012 | Meloni | G01N 21/6489 250/459.1 |

* cited by examiner

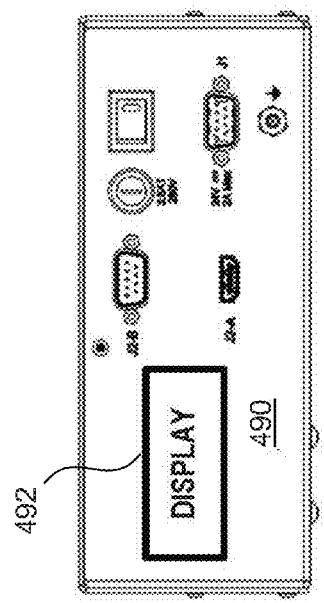
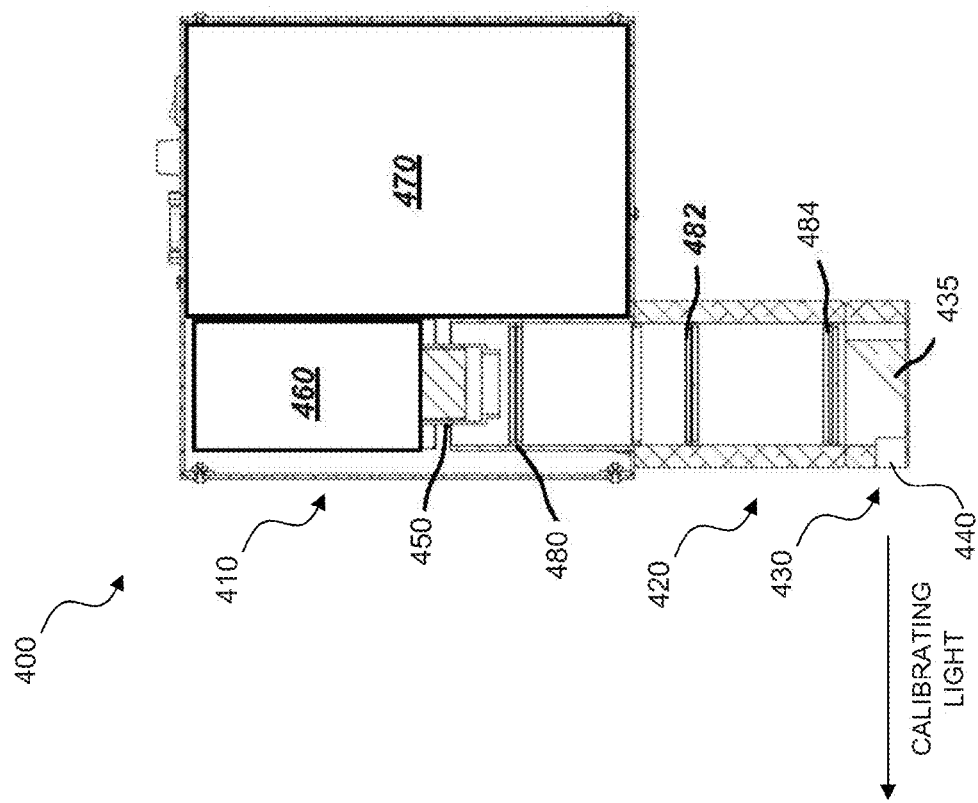
FIG. 4B
FIG. 4A

SYSTEM AND METHOD FOR CALIBRATION OF OPTICAL SIGNALS IN SEMICONDUCTOR PROCESS SYSTEMS

CROSS-REFERENCE TO RELATED APPLICATION

This application claims the benefit of U.S. Provisional Application Ser. No. 62/456,424, filed by Kueny on Feb. 8, 2017, entitled "SYSTEM AND METHOD FOR IN-CHAMBER CALIBRATION OF OPTICAL SIGNALS," and U.S. Provisional Application Ser. No. 62/421,862, filed by Kueny on Nov. 14, 2016, entitled "A SYSTEM AND METHOD FOR IN-CHAMBER CALIBRATION OF A FIBER OPTIC COUPLED SPECTROMETER," commonly assigned with this application and incorporated herein by reference.

TECHNICAL FIELD

This disclosure relates generally to optical measurements for semiconductor processing systems including optical emission spectroscopy and/or optical reflectometry subsystems. More particularly, the disclosure relates to a system, method and software program product for simulating, monitoring, analyzing and calibrating the optical system properties and components used during detection of optical emission signals from a plasma-based wafer processing system.

BACKGROUND OF THE DISCLOSURE

Selectively removing or depositing materials on a semiconductor wafer to form integrated circuit structures from wafers is well known in the art of semiconductor processing. Removal of material from a semiconductor wafer is typically accomplished by employing some type of etching process, such as, reactive ion etching or atomic layer etching. Depositing material on a wafer may involve processes such as chemical and physical vapor deposition (CVD/PVD), molecular beam epitaxy (MBE) or atomic layer deposition (ALD). In semiconductor processing, other plasma-based or emitting processes such as implantation are also known and optically monitored. All such processes are tightly controlled and are done in an environmentally controlled process chamber. Because exact amounts of material are to be deposited onto or removed from the surface of a wafer, the deposition or removal progress must be continually and accurately monitored to precisely determine the endpoint or characteristic state of a particular process.

Optically monitoring the chamber process is one very useful tool for determining the processing status, processing state conditions or endpoint for an ongoing process. For instance, the conditions interior to the chamber may be optically monitored for certain known emission lines by analyzing predetermined wavelengths of light emitted or reflected from within the chamber. Conventional optical monitoring methods include optical emission spectroscopy (OES), absorption spectroscopy, reflectometry, interferometric endpoint (IEP), etc.

OES is widely used in the semiconductor industry for monitoring the state of a wafer process within a process chamber by measuring and characterizing the plasma optical emission generated within the process chamber. While OES techniques may vary with the particular application and process, typically the optical emission intensities are monitored at one or more predetermined wavelengths. Monitored processes include semiconductor etching, deposition, implantation and other processes where film thickness and plasma/wafer emission monitoring is applicable. Additionally, chamber conditions independent of or combined with the wafer conditions, may be monitored. Depending on the process, various algorithms may be employed for deriving parameters from the optical signal intensities that are useful in assessing the state of the semiconductor process and the processed wafer, detecting faults associated with the process, chamber or other equipment and even the condition of interior surfaces of the plasma chamber.

SUMMARY

In one aspect, the disclosure provides an optical calibration device for in-chamber calibration of optical signals associated with a processing chamber. In one example, the optical calibration device includes: (1) an enclosure, (2) an optical source located within the enclosure and configured to provide a source light having a continuous spectrum, and (3) optical shaping elements located within the enclosure and configured to form the source light into a calibrating light that approximates a plasma emission during an operation within the processing chamber.

In another aspect, the disclosure provides a characterization system for plasma processing chambers. In one example, the characterization system includes: (1) an optical calibration device positioned within a plasma processing chamber having a viewport, (2) an optical coupling system coupled to the viewport and positioned to receive calibrating light emitted by the optical calibration device, and (3) a spectrometer optically coupled to the optical calibration device via the optical coupling system and configured to generate and report measured optical signal data associated with the calibrating light and propagation of the calibrating light through the plasma processing chamber, the viewport, and the optical coupling system.

In yet another aspect, a method of characterizing plasma processing chambers is disclosed. In one example, the method of characterizing plasma processing chambers includes: (1) positioning an optical calibration device within a plasma processing chamber having a viewport, (2) coupling an optical coupling system to the viewport, the optical coupling system positioned to receive calibrating light emitted by the optical calibration device, (3) coupling an optical detector to the optical calibration device via the optical coupling system, and (4) configuring the optical detector to generate and report measured optical signal data associated with the calibrating light and its propagation through the plasma processing chamber, the viewport and the optical coupling system.

Another example of a method of characterizing plasma processing chambers is provided. In this example the method includes: (1) determining a first reference intensity ratio and a first operational intensity ratio of a reference plasma processing chamber, (2) determining a second reference intensity ratio and a second operational intensity ratio of a second plasma processing chamber, and (3) determining a characterization ratio of emitted light from the reference and second plasma chambers using a mathematical combination of the first and second reference intensity ratios and the first and second operational intensity ratios.

In still a different aspect, the disclosure provides a chamber characterizer. In one example, the chamber characterizer includes a non-transitory computer readable medium having a series of instructions stored thereon that when executed cause a processor to: (1) determine a first reference intensity ratio and a first operational intensity ratio of a reference plasma processing chamber, (2) determine a second reference intensity ratio and a second operational intensity ratio of a second plasma processing chamber, and (3) determine a characterization ratio of emitted light from the reference and second plasma chambers based on a mathematical combination of the first and second reference intensity ratios and the first and second operational intensity ratios.

BRIEF DESCRIPTION OF THE DRAWINGS

The disclosure may be understood by reference to the following detailed description taken in conjunction with the drawings briefly described below.

FIG. 4A and FIG. 4B show multiple views of an embodiment of an optical calibration device constructed according to the principles of the disclosure that is suitable for placement into a processing chamber.

DETAILED DESCRIPTION

Figure 1:
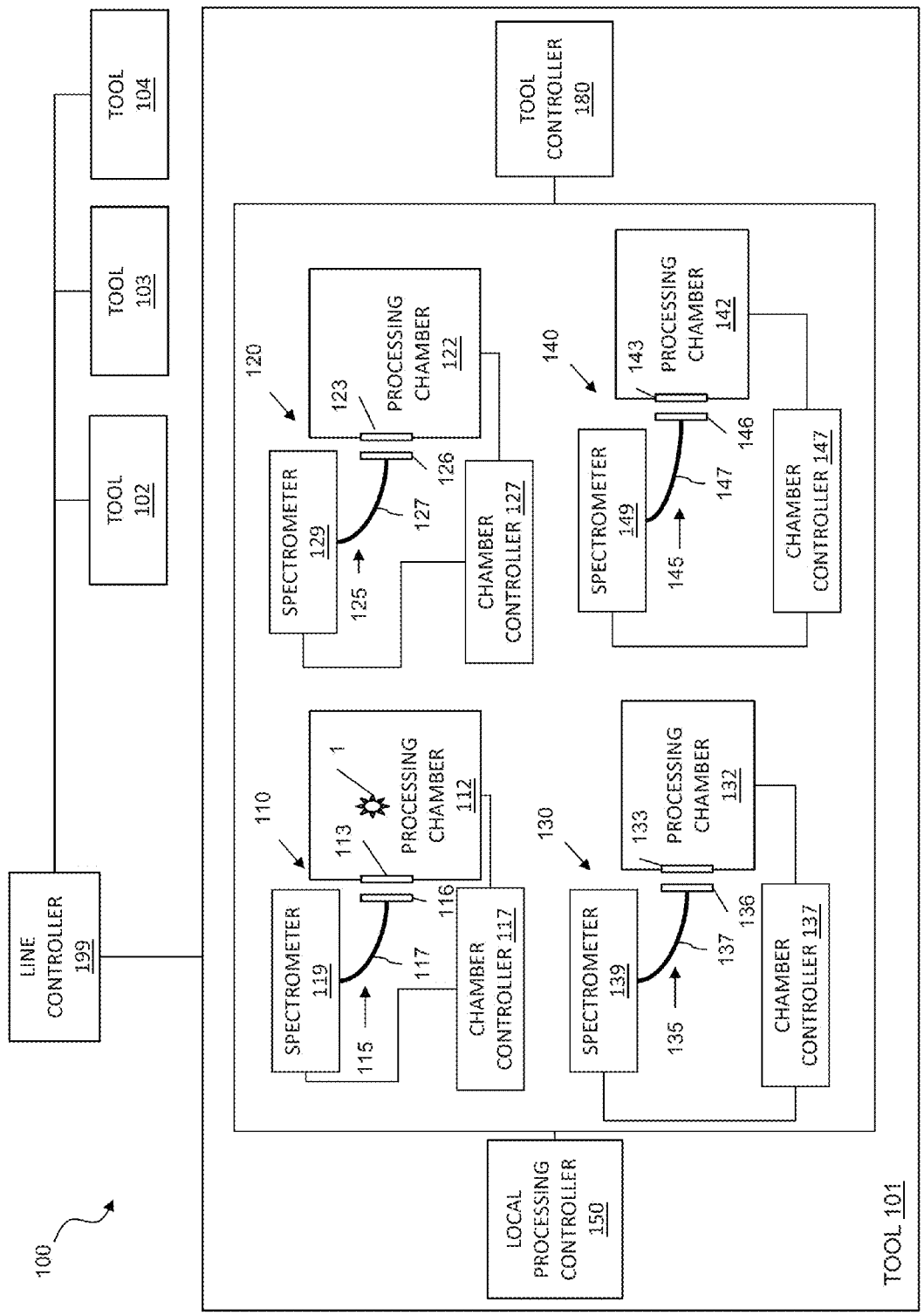
FIG. 1 is a block diagram of a processing system, having multiple plasma processing chambers and spectroscopic monitoring equipment, constructed according to the principles of the disclosure.

In the following description, reference is made to the accompanying drawings that form a part hereof, and in which is shown by way of illustration, specific embodiments in which the invention may be practiced. These embodiments are described in sufficient detail to enable those skilled in the art to practice the features disclosed herein, and it is to be understood that other embodiments may be utilized. It is also to be understood that structural, procedural and system changes may be made without departing from the spirit and scope of the present invention. The following description is, therefore, not to be taken in a limiting sense.

For clarity of exposition, like features shown in the accompanying drawings are indicated with like reference numerals and similar features as shown in alternate embodiments in the drawings are indicated with similar reference numerals. Other features of the present invention will be apparent from the accompanying drawings and from the following detailed description. It is noted that, for purposes of illustrative clarity, certain elements in the drawings may not be drawn to scale.

A customary way to monitor the optical signals from a semiconductor plasma processing chamber is to use an optical monitoring system which consists of an array-based optical spectrometer and an optical coupling system to bring the light from the plasma in the interior of the chamber to the spectrometer. The optical spectrum is often recorded as a series of light intensity measurements in a set of narrow spectral bands, typically repeated at specific time intervals.

The spectra recorded by a spectrometer are influenced by factors other than the properties of the light emitted by the plasma. These factors include the wavelength and intensity calibrations of the spectrometer and the state and transmission properties of the optical coupling system. To provide accurate monitoring of a chamber, the monitoring system should be calibrated along the entire optical path from the source light volume (e.g., light emitting plasma) inside the chamber to the analog or digital final output of the recording spectrometer. Although individual components may be independently characterized, assembly processes and changes following from use can alter the transmission properties.

The recorded spectra obtained by the spectrometers can also be influenced by the characteristics, such as geometry, cleanliness and wear, of the processing chambers. It is often desirable to recreate (in multiple independent chambers) as nearly as possible a set of conditions in a plasma environment, such as for etching, deposition, implantation, or other purposes common in the semiconductor industry. In the semiconductor industry it is often advantageous to have indistinguishable ("matching") processes in multiple processing chambers to insure the same processing regardless of chamber used. It can also be helpful to return a process chamber to a particular state it transitioned from at some point in the past following maintenance or other interruptions.

As described herein, OES can be employed for characterizing plasma processing chambers during operation. The optical emission from plasma contains contributions from many distinct atomic and molecular states. The identity and the relative amplitude of these emissions is a sensitive indicator of the precise state of the plasma and the chamber in which the plasma exists. Therefore, by monitoring, recording, analyzing and comparing these details of the optical spectrum from plasma chambers, an operator or automated system controller can adjust a chamber or chambers, to assist in obtaining indistinguishable processing steps in multiple chambers.

Thus, the disclosure recognizes that in a plasma processing chamber, the analysis of the light emitted from the plasma can provide important information about the operating conditions of the chamber and associated process chamber control elements. Measurement of the ratio of the energy emitted into different spectral lines from the same atom, for example, can give information about the electron temperature in the plasma. Many other features of observed spectra such as spectral intensities, spectral line widths, and band edge locations may also provide critical information as to the plasma and chamber state or conditions. It is common for these chambers to be equipped with optical windows and spectrometers to monitor the plasma. However, in the case of spectral line intensities, the energy ratio cannot be obtained by simply measuring the ratio of the corresponding peaks in the signal recorded by the spectrometer. The light has to pass through a window and also collection optics including a fiber optic cable to get to the spectrometer. These items can attenuate the light differently at different wavelengths. Also, the spectrometer sensitivity (signal per unit of optical energy incident at a given wavelength) is typically not uniform, and not necessarily known.

In order to compensate for these effects, the disclosure recognizes that it would be advantageous to have a standardized light source, suitable for use within a processing chamber, for which spectral characteristics, such as the ratio of energy emitted into different wavelength bands or broadband spectral intensities, are known or determinable in absolute or relative quantities. This light source could be placed inside the processing chamber, so that the light would take substantially the same path to the spectrometer as the plasma emission of interest. This light source can therefore be a substitute for the plasma and the light that it emits. Optical signal data can be obtained from the standardized light source for characterizing processing chambers based upon a "constant" standardized light source rather than the plasma emitted light, which is not independent of the chamber or process to be refined.

By way of example, the optical signal data can include a ratio of signals measured (as modified by transmission and recording) from the standardized light source in different wavelength bands that can be related to the true (known) energy ratios characteristic of the standardized light source. The relationships established in this way could then be used to convert the measured ratios of signals from the plasma into the desired energy ratios for characterization for one or more process chambers and their plasma conditions.

As such, the disclosure provides a method of characterizing and comparing processing chambers employing an OES system that can be employed for process chamber matching. Thus, the optical spectrum is used as a part of a feedback system for control and/or initial configuration of the plasma in process chambers for uniform processing. In one embodiment, the disclosed method and system enable an operator to characterize the operation of a processing chamber by measuring the ratio of signals for different spectral lines and calculating an intensity ratio therefrom that can be used by an operator or the system controller to adjust the energy level, plasma temperature or other process parameter of a plasma in a chamber for chamber matching. Commonly modified control parameters impacting the plasma conditions include gas partial pressures, gas total pressure, gas flow rates, RF power input level, and RF match conditions. In certain cases, it is not a control parameter that may be identified and modified but may be an actual component of the plasma system or optical system. For example, an optical window may be contaminated with a deposited film or a chamber "showerhead" may be eroded by use and alter observed optical signals. The system and method can be employed to align the processing steps in the multiple chambers of a processing line, such as illustrated in FIG. 1.

Figure 9:
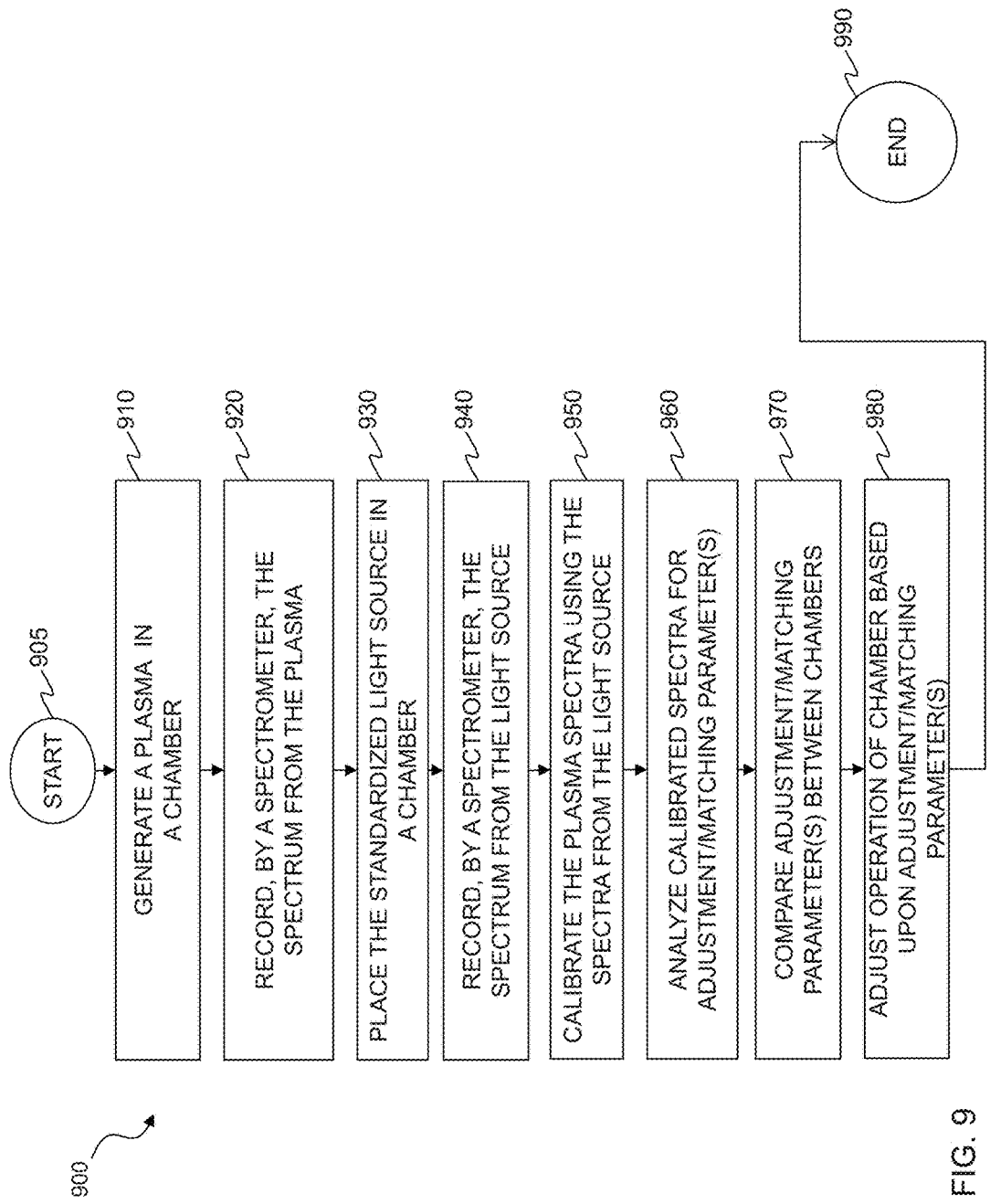
FIG. 9 is a flow chart of an embodiment of a method of characterizing and matching process chambers, carried out according to the principles of the disclosure.

FIG. 1 illustrates a block diagram of an embodiment of a processing line 100 having multiple plasma processing chambers and spectroscopic monitoring equipment constructed according to the principles of the disclosure. FIG. 1 illustrates an environment where a calibration system or method, as disclosed herein, can be employed to obtain or at least assist in obtaining uniform processing conditions across multiple processing chambers. Processing line 100 includes four tools, tools 101, 102, 103, and 104, and a line controller 199. The processing line 100 may be a subset of a larger portion of an etch processing line of a semiconductor fabrication plant (fab). As such, the line controller 199 can be a fab or process line server. Tool 101 is illustrated and discussed in detail below as a representative of the other tools 102, 103, and 104. It should be noted that according to the process chamber matching disclosed herein, all processing chambers of tools 101-104 may be matched or select chambers of each tool may be matched in subgroups. For example, processing chamber 112 of tool 101 can be matched to equivalent processing chambers of tools 102-104. The methods illustrated in FIG. 9 and FIG. 10 are an example of process chamber matching that can be employed.

The processing line 100 illustrates a distributed control system wherein the control logic for matching of the various chambers/modules of processing line 100 may be located in multiple devices. One skilled in the art will understand that the control logic can be located in multiple or even single components of the processing line 100. For example, portions of control logic for semiconductor processing can be distributed across spectrometers, chamber controllers, local processing controllers, tool controllers, and the line controller 199. In one embodiment of chamber matching, coordination must be established between these multiple entities for identification, data transfer, data processing and analysis. The tool 101 includes multiple processing chambers—spectrometer pairs that are denoted as monitored processing modules 110, 120, 130, and 140. The processing chambers of the monitored processing modules 110, 120, 130, 140, are configured to process wafers to form integrated circuits and the spectrometers are used to monitor the processing.

For example, during normal semiconductor processing the monitored processing modules 110, 120, 130, 140 employ an OES system to monitor and/or control the state of a plasma process within each plasma processing chamber. Each of the monitored processing modules 110, 120, 130, 140, include a processing chamber that generally encloses a wafer and process plasma in a partially evacuated volume which may include various process gases. Light is detected from the plasma at a viewport and guided via an optical coupling system to an optical detector. Detected light may range over the wavelength range from Deep Ultraviolet (DUV) to Near-infrared (NIR) (typically less than 200 nm to greater than 1700 nm) and wavelengths of interest may be selected from any subrange therein. The viewport is commonly formed from sapphire or quartz materials supporting a wide range of wavelength transmission. An optical coupling system may include multiple types of optical elements such as, but not limited to, optical filters, lenses, mirrors, windows, apertures, fiber optics, etc.

The optical detector is commonly a spectrometer but may also be a monochromator or photodiode-based detector. For post detection and conversion to electrical signals, optical signals are typically amplified, digitized within a subsystem of the optical detector and passed to a signal processor. The signal processor may be for example an industrial PC, PLC or other system which employs one of more algorithms to produce output such as an analog or digital control value, for example, representing the intensity of a specific wavelength or the ratio of two wavelength bands. The algorithm can analyze emission intensity signals at predetermined wavelengths and determine trend parameters that relate to the state of the process and can be used to access that state, for instance end point detection, etch depth, plasma conditions, etc. The output values may be transferred to the processing chambers for monitoring and/or modifying the production process occurring within the processing chambers.

More specifically, the tool 101 includes a local processing controller 150 that is configured to receive monitoring data from coupled spectrometers and control the plasma processing of corresponding processing chambers based thereon. The local processing controller 150 can be configured to perform the functions typically performed by endpoint controllers. The monitored processing modules 110, 120, 130, and 140 are coupled to the local processing controller 150 via conventional communication connections such as USB, RS232 and/or Ethernet (not shown). In some embodiments, the tool 101 can include multiple local processing controllers (e.g., one per monitored processing module).

Local processing controller 150 may be communicatively coupled to tool controller 180, line controller 199 and spectrometers 119, 129, 139 and 149 (not all connections are shown in FIG. 1). The tool controller 180 monitors and directs the operation of the tool 101. The line controller 199 can be located remote from the other devices of the processing line 100. In one embodiment, the line controller 199 is a server, such as a fab server, that is communicatively coupled to the local processing controller 150 via a communication network, such as Ethernet. The line controller 199 is also communicatively coupled to a tool controller 180 of the tool 101. Conventional connections can be used for the communicative coupling between components of the processing line 100.

The tool controller 180 receives feedback from components of the tool 101 and directs operation of the coupled processing chambers of the tool 101 based on the feedback. In various embodiments, the tool controller 180 can receive feedback data from the local processing controller 150, the line controller 199, or both. The feedback data can be a processing chamber adjustment based on a characterization intensity ratio determined by either the line controller 199, the local processing controller 150, one of the spectrometers or chambers controllers of the tool 101, or a combination of any of these devices. In FIG. 1, the various processing chambers are denoted as processing chambers 112, 122, 132, 142, the corresponding chamber controllers 117, 127, 137, 147, and the corresponding spectrometers are denoted as spectrometers 119, 129, 139, and 149.

Using monitored processing module 110 as an example for the other monitored processing chambers, processing chamber 112 is used to contain a wafer as it is modified by process plasma. Optical emissions from the plasma can contain information regarding the state of the wafer as well as the conditions of plasma and the overall functioning of the processing chamber 112 and associated processes module 110. For example, the optical emissions can carry information about the state of an etch via emission of reactant and product species from the process gasses and the wafer materials as well as plasma properties such as plasma temperature and density and functional health of the process chamber itself.

Each of the processing chambers 112, 122, 132, 142, includes a viewport 113, 123, 133, 143, respectively. One skilled in the art will understand that the processing chambers 112, 122, 132, 142, can be the same or different type of processing chamber and include additional components that are not illustrated or discussed herein. Additionally, one skilled in the art will understand that the tool 101 can include more or less processing chambers or modules as illustrated herein. In the illustrated embodiment, the tool controller 180 directs at least a portion of the operation of the processing chambers 112, 122, 132, 142.

Each of the spectrometers 119, 129, 139, 149, receive optical signals from their corresponding process chambers and disperse the light into a spectrum. Each of the spectrometers 119, 129, 139, 149, includes an optical detector that receives the spectrum and converts the spectral light into raw spectral intensity data (otherwise referred to as uncalibrated spectral data). With information of the spectral output of a standardized light source, the spectrometer can be calibrated to those values. Details of calibrating spectrometers may be found for example in U.S. Pat. No. 8,125,633 included herein by reference.

As used hereinafter, the term "spectrometer" should be understood as generally comprising at least a spectrographic component for dispersing light into a spectrum, an optical detector for converting spectral light from the spectrographic component to raw (uncalibrated) spectral intensity data and computational electronics, firmware and processing capacity for executing software performing measurements, calibrating the measurements and converting the raw spectral intensity data into optical signal data. The optical signal data can be used as optical calibrating data, i.e., calibration data. Thus, a typical spectrometer will include at least one optical port, optical coupler or other optical component for receiving light, and one or more data connections, ports or other data transmission component for sending and receiving data and executable program code.

Each of the spectrometers 119, 129, 139, 149, are optically coupled to their respective processing chamber via an optical coupling system, denoted in FIG. 1 as optical coupling system 115, 125, 135, 145. Each of the optical coupling systems 115, 125, 135, 145, includes an optical fiber 117, 127, 137, 147, and an optical coupler 116, 126, 136, and 146. The optical couplers are optically coupled to their respective viewports of associated processing chambers. The optical couplers 116, 126, 136, 146, may include optical components such as lenses or opto-mechanical components such as positioners. In some embodiments, the optical coupling systems 115, 125, 135, 145, also include a mode scrambler (not shown in FIG. 1). The mode scramblers can be a diffuser that is placed in front of the fiber entrance face. In some embodiments, the mode scramblers can be a fine grid that is placed in front of the fiber entrance face. Alternatively, grooves can be formed in the fiber, such as described in U.S. Pat. No. 4,676,594.

During a down time of the monitored processing modules 110, 120, 130, 140, such as during scheduled maintenance when no normal semiconductor processing is being performed, a standardized light source can be positioned within the processing chambers 112, 122, 132, 142, to allow the respective spectrometers to record and process optical calibration data such as a full spectrum transmission measurement or intensity ratio based on two designated wavelengths. In one embodiment, the intensity ratio is an integrated peak area ratio between the pair of spectral lines from wavelengths selected to be within a corresponding wavelength range of a plasma used in the processing chambers 112, 122, 132, 142, during operation. Furthermore, the net area of the spectral line peaks is calculated to determine the intensity ratio. The integrated peak area ratio can be calculated using a spectrum of the predetermined wavelengths as defined by the spectrometers. The intensity ratio can be used to control each processing chamber in such a way as to tune the electron temperature in the plasma of the processing chambers to obtain uniform processing.

In FIG. 1, a standardized light source 1 is shown positioned in processing chamber 112 as an example. The standardized light source 1 can be an optical calibration device as disclosed herein and may be connected with spectrometer 119, local processing controller 150 and other systems for control and configuration. The standardized light source 1 can be used to determine optical signal data for chamber characterization and chamber matching. The optical signal data can include, for example, a reference intensity ratio for processing chamber 112 and then be used to determine the reference intensity ratios for processing chambers 122, 132 and 142. In this example, the processing chamber 112 is a reference chamber which as used herein is a well characterized process chamber that is understood as a baseline or chamber of record. An operational intensity ratio for each of the processing chambers 112, 122, 132, 142, can then be similarly determined without the standardized light source 1 during operation of the processing chambers. The same wavelengths are used to determine both the reference intensity ratios and the operational intensity ratios. Standardized light source 1 is positioned in each of processing chambers 112, 122, 132, and 142 to determine optical signals for each chamber and optical system configuration.

Analysis between the reference and operational intensity ratios may be used to indicate differences in the plasma and/or chamber state amongst the measured chambers/modules. A characterization ratio can then be determined for any pair of processing chambers based on the reference and operational intensity ratios. Based on the characterization ratio, the tool controller 180, for example, can adjust processing chambers to obtain uniform processing. An embodiment of a method for determining the intensity ratios and the characterization ratio is detailed below.

Figure 2B:
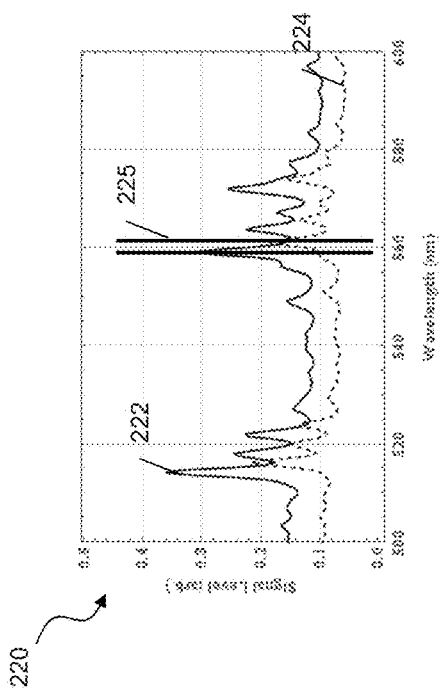
FIGS. 2A, 2B, 2C, and 2D show a set of plots indicating common problems and observables associated with an optical system used with a semiconductor processing system.
Figure 2D:
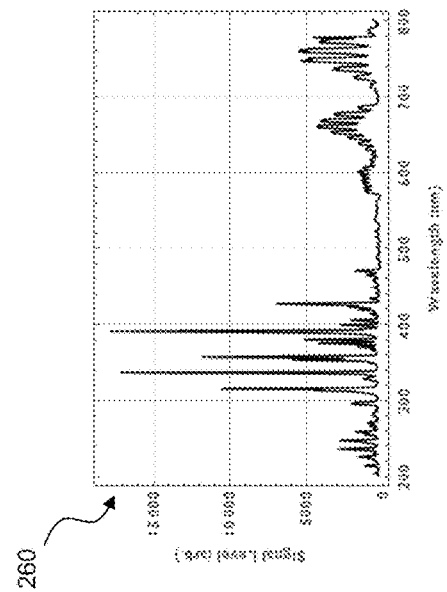
Figure 2A:
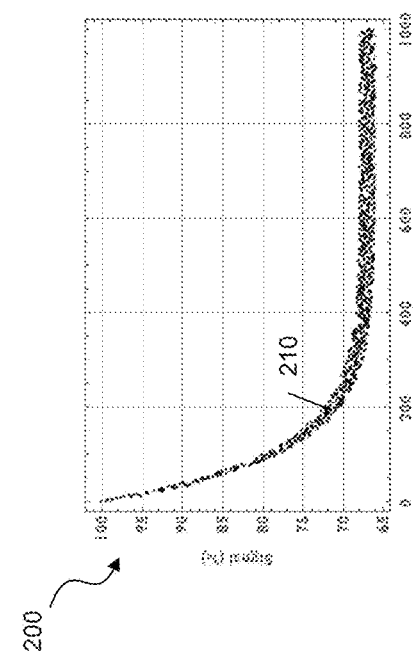

FIGS. 2A, 2B, 2C, and 2D show a set of plots indicating common problems and observables associated with OES optical system matching, in accordance with an embodiment of the disclosure. In FIG. 2A, plot 200 indicates optical signal drift observed during plasma processing. Curve 210 may represent an observable related to the plasma processing of the wafer and/or the state of the plasma or chamber. One very common root cause of observed drift is window clouding and/or optical fiber solarization. This drift is generally dependent upon wavelength and different portions of measured spectra are variously impacted.

Additionally, curve 210 may be convolved with signal offset and/or wavelength calibration shift as indicated in plot 220 of FIG. 2B. Comparing representative spectral curves 222 and 224, it may be seen that either or both causes (signal offset, calibration shift, indicated by lines 225) may also be contributors to the observation of drift. Convolution of plasma process related signal changes and signal changes due to differing/changing optical system components complicates process control and chamber matching by obscuring specific causes. Measurements taken using a standardized light source may assist in differentiation and identification of specific root causes as discussed further in association with FIG. 10.

Figure 2C:
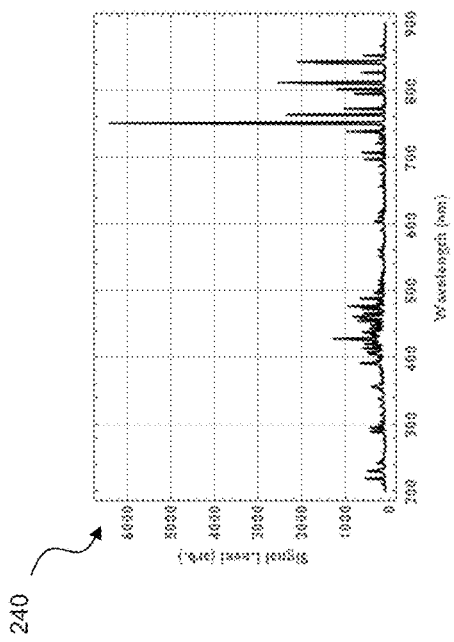

Plot 240 of FIG. 2C indicates a typical Argon plasma emission spectrum where multiple strong atomic emission lines may be observed. It is well known that plasma temperature and other parameters may be deduced from the comparison of specific spectral lines using determined line intensity ratios, known Einstein coefficients and Saha and/or Boltzmann formulae. Pure gasses may be used in these determinations as gas mixtures add further complications from quenching and other factors.

Plot 260 of FIG. 2D indicates a typical Nitrogen plasma emission spectrum where both atomic and molecular emission lines may be observed. The various lines may be related to the various activation and ionization states of the nitrogen diatomic gas, spectral line broadening, band edge shift and location, intensity amplitudes, rotational and vibrational states. The ro-vibrational states may be useful in understanding the ionization fraction and its impact upon etching/processing characteristics. Any of these spectral features may be analyzed, processed, parameterized and used for chamber matching control, such as adjustment or matching parameters.

However proper determination of line intensity ratios and other metrics require the relative or absolute calibration of optical signals and the isolation from systematic factors modifying the "true" signals from the plasma. Optical system components, including but not limited to, viewports, optical filters, fiber optical cable system and optical detector systems each potentially contribute to the mis-interpretation of optical signal changes and both absolute and relative optical signal values. For example, differently contaminated viewports may uniformly attenuate the optical signal from different chambers by differing amounts and lead to an improper conclusion that the state of the plasma is different between the chambers. Similarly, solarization of optical fibers may attenuate portions of the optical spectrum by differing amounts and lead to an improper conclusion that the process gas excitation conditions are different between chambers. Furthermore, transient solarization may lead to the incorrect conclusion that for any one chamber the plasma conditions are drifting over time.

For optical detectors such as spectrometers, the overall response depends on the sensitivity of the spectrometer, which can vary unit to unit, as well as the transmission of various optical elements between the chamber and the spectrometer. By measuring the spectrum generated by a reference/calibration standardized light source through these elements, the combined effect of these elements on the spectrometer's output signal may be compared to a reference spectrum or other data. This permits an optical signal level correction to be determined that may be used to bring the system response to a more accurate value. The in-chamber calibration enables the use of the spectrometer in applications where quantitative measurement is important. For the above mentioned reasons and others, it is valuable to be able to perform full-spectrum calibration of optical signal from one or more chambers for the purposes of determining within-chamber variation and inter-chamber matching.

Figure 3:
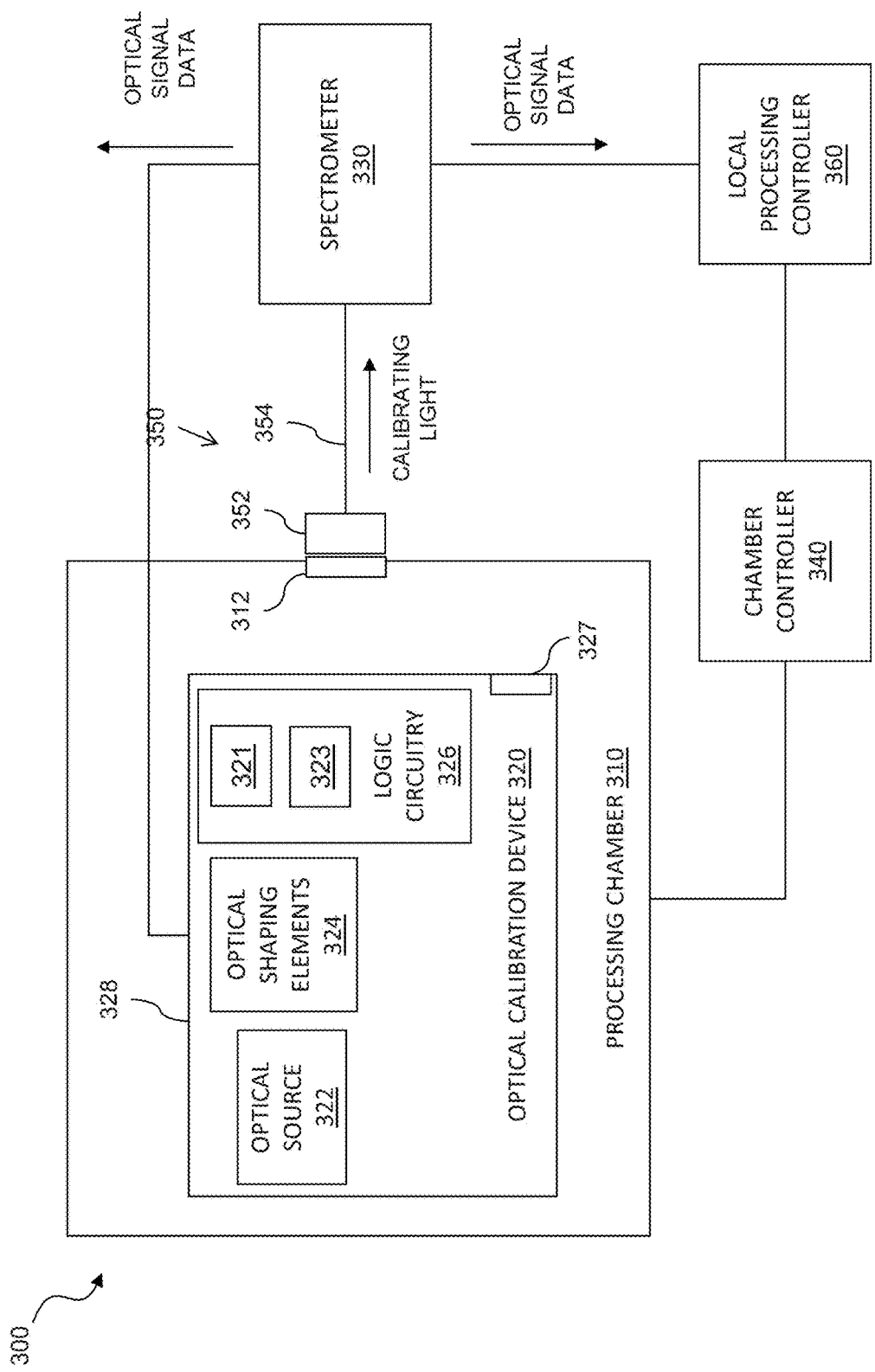
FIG. 3 shows a block diagram of an embodiment of a characterization system constructed according to the principles of the disclosure that is useful for calibrating and/or referencing optical signals used for monitoring and/or controlling the state of a light emitting process within a processing chamber.

FIG. 3 illustrates a block diagram of an embodiment of a characterization system 300 useful for calibrating/referencing optical signals to monitor and/or control the state of a plasma process within a plasma processing chamber. The characterization system 300 is used with a processing chamber 310 having a viewport 312, such as one of the processing chambers 112, 122, 132, 142, of FIG. 1. The characterization system 300 includes an optical calibration device 320, a spectrometer 330, a chamber controller 340, an optical coupling system 350, and a local processing controller 360.

The optical calibration device 320 is configured to provide a calibrating light that approximates a plasma emission during an operation within the processing chamber 310. In approximating the plasma light, the calibrating light from the optical calibration device 320 provides a light field that includes, at least, a similar wavelength range, spatial and angular extent to that provided by the plasma and observed by the optical system. The optical calibration device 320 is robust, portable, and sufficiently compact to be positioned within the processing chamber 310. The optical calibration device 320 is positioned within the processing chamber 310 to provide the calibrating light to the optical coupling system 350 via the viewport 312. The optical calibration device 320 includes, at least, an optical source 322, optical shaping elements 324, logic circuitry 326, an interface panel 327, and an enclosure 328.

The optical source 322 is located within the enclosure 328 and is configured to provide a source light that is used to provide a calibrating light. In one embodiment, the optical source 322 has the property that the irradiance in any spectral band is repeatable throughout its calibration lifetime for stability of the calibration system without the need for constant re-calibration/certification of the source. Additionally, the optical source 322 can provide a source light with a continuous emission spectrum so that optical signals for calibration are available for any wavelengths within the range of the spectrometer 330. As seen in the plots of FIGS. 2A-2D emissions can occur over wide ranges of wavelength.

In various embodiments, the optical source 322 differs from typical radiometric calibration light sources that are based on Quartz Tungsten Halogen (QTH) technology that have the disadvantages of: 1) having a short useful life (recalibration is typically required after 50 hours of use), 2) a warm-up period is usually required and 3) high power requirements, especially if short wavelengths are required.

Considering these disadvantages, in one embodiment the optical source 322 can be a xenon flashlamp such as a Series 1100 flashlamp from Excelitas or another type of flashlamp that produces light in an approximately microsecond optical pulse. These type of flashlamps typically have a useful lifetime of a hundred or more million flashes. Experimentation has shown that after an initial burn-in period, on the order of a million flashes, their energy output becomes consistent enough to serve as a calibration standard. Though the flash energy can fluctuate from flash to flash, a small number of flashes can be averaged to provide a spectral brightness which is repeatable to within a percent or so and remains true over a sequence of many tens of thousands of flashes with very limited warm-up cycling/flashing. A typical number of flashes used for measurement ranges from approximately ten to a few hundred. The optical signals generated from the flashlamp may be integrated within a spectrometer optically on the optical detector and may be averaged after conversion in a digital form. The xenon flashlamp typically does not age except when it is fired. The useful life of this type of light source, therefore, can be advantageously long when used as part of a chamber characterization system. A flashlamp has the additional advantage that it can be used in the presence of ambient room light, by trigger and alternating flash-on and flash-off measurements and subtracting. These alternating flash-on and flash-off measurements may be recorded by a spectrometer (e.g., spectrometer 330) and mathematically processed within the spectrometer or within some other processing system such as a connected computer (e.g., chamber controller 340)

The optical shaping elements 324 are located within the enclosure 328 and are configured to form the source light into the calibrating light that approximates a plasma emission during an operation within the processing chamber 310. Approximating a plasma emission is wherein the calibrating light has a wavelength range, spatial extent and angular extent at least equal to that provided by a plasma emission within the processing chamber 310 and observed by an optical detector, such as the spectrometer 330. A combination of the optical source 322, the optical shaping elements 324, and placement of the optical source 322 or optical calibration device 320 within the processing chamber 310 can cooperate to achieve an approximation of the plasma emission. The optical shaping elements 324 can include diffusers, baffles, lenses, mirrors, apertures, filters, windows, and other known optical components that cooperate to form the source light into the calibrating light. In one embodiment, the optical shaping elements 324 include at least one diffuser and one baffle. The calibrating light generated by the optical shaping elements is a light field of a spatial, angular and spectral form suitable for calibration. Typical requirements for the calibrating light include sufficient spatial extent to fill any physical apertures of the optical path from the plasma volume to the spectrometer 330, sufficient angular extent to fill the numerical aperture of the optical path (the optical path may be considered limiting as the plasma emits into all solid angles) through the optical coupling system 350 and a spectral range covering wavelengths of emission of interest.

The logic circuitry 326 is configured to control operation of the optical source 322 in accord with commands and data transmitted to/from, for example, the spectrometer 330, the chamber controller 340, and/or the local processing controller 360. For example, the logic circuitry 326 can include the trigger assembly, memory for data, communication circuitry and a command processor for the optical calibration device 320. Communication circuitry 321 and an accessible memory 323 (e.g., accessible via the interface panel 327) are denoted in the logic circuitry 326 in FIG. 3. The memory 323 can store data used for calibration and chamber matching such as, calibration data, optical signal data associated with calibration light and a plasma emission, and spectrum data such as reference spectrum and factory measured spectrum. The interface panel 327 can be communicatively and electrically coupled to the logic circuitry 326 and includes connectors for interaction between the optical calibration device 320 and external systems to communicate, for example, firing signals, timing signals, and identification data transfer (serial numbers, factory-provided calibration spectra etc.). The communication circuitry 321 of the logic circuitry 326 can be used to direct the transfer of information. The external systems include, for example, the spectrometer 330, the chamber controller 340, the local processing controller 360, and/or other computing or processing devices that are different than or external to the optical calibration device 320. Data collected by the spectrometer 330 may combine identifying information of both the processing chamber 310 (via the chamber controller 340 or other means) and from the optical calibration device 320. These data define the state of the larger characterization system 300 and include, at least, chamber identifying information, spectrometer identifying information, and calibration device identifying information. FIGS. 4A and 4B illustrate one embodiment of an optical calibration device that can be used in a processing chamber such as processing chamber 310.

Figure 5:
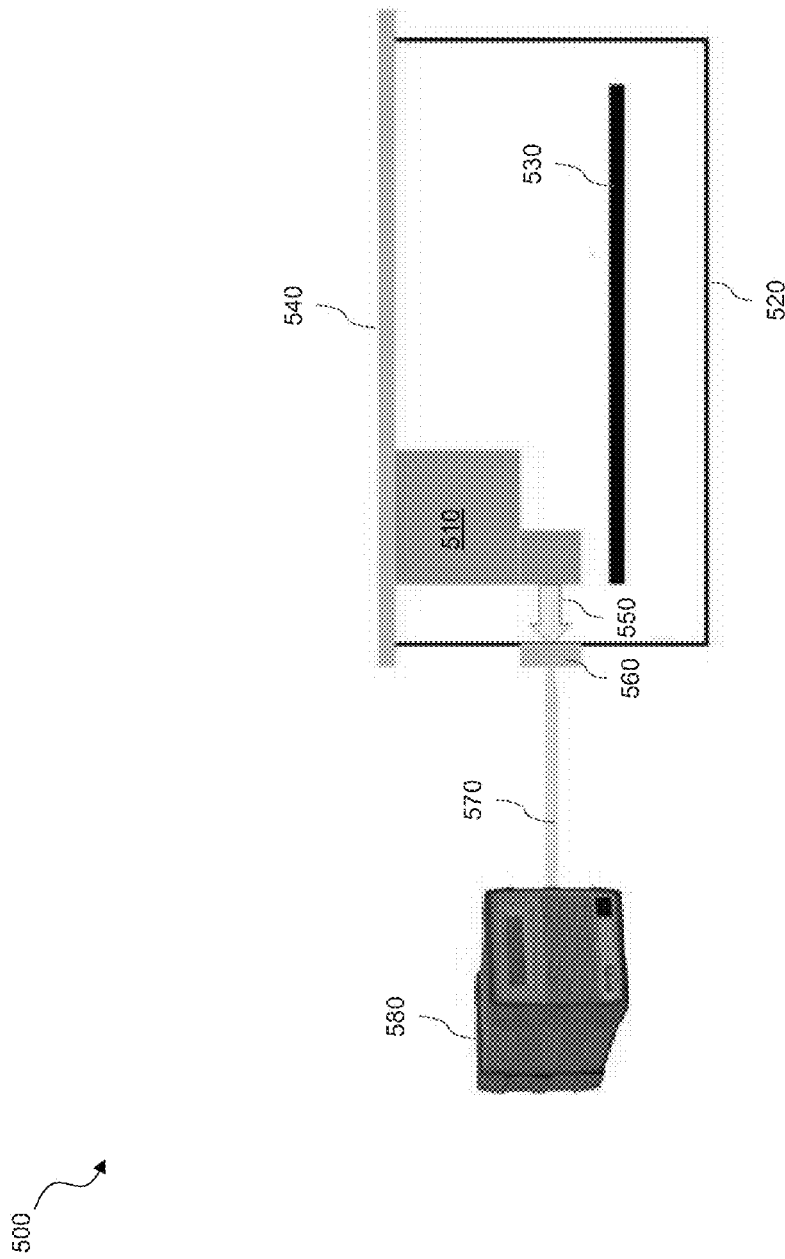
FIG. 5 shows a pictorial schematic representing an example configuration for orientating and mounting an optical calibration device into a processing chamber, according to the principles of the disclosure.

The enclosure 328 contains and protects the various components of the optical calibration device 320. The enclosure 328 can also allow communication with the optical calibration device 320 via the interface panel 327 and an opening for the calibrating light via an exit port. The enclosure 328 can include a main body and an extended body, wherein at least a portion of the optical shaping elements 324 are located within the extended body. The enclosure 328 can be made of a rigid material, such as a metal, to protect the optical calibration device 320. The enclosure 328 can also include mounting hardware to secure the optical calibration device 320 within the processing chamber 310 at specific predetermined locations appropriate for illuminating the optical viewport 312 of the processing chamber 310 and subsequent optical elements including the optical coupling system 350 and the spectrometer 330. FIG. 5 illustrates an example of mounting an embodiment of an optical calibration device, such as the optical calibration device 400, within a processing chamber. In addition to the illustrated components, the optical calibration device 320 can include other components, such as a mirror. The mirror can be used to direct the calibrating light to an exit port of the enclosure 328.

The optical coupling system 350 is optically coupled to the viewport 312 and positioned to receive the calibrating light emitted by the optical calibration device 320. The optical coupling system 350 includes an optical coupler 352 and a fiber optic cable 354. The optical coupling system 350 can also include other components, such as a mode scrambler.

The spectrometer 330 is optically coupled to optical calibration device 320 via the optical coupling system 350 and is configured to generate and report measured optical signal data associated with the calibrating light and propagation of the calibrating light through the processing chamber 310, the viewport 312, and the optical coupling system 350.

In general, optical signal data includes one or more optical intensity spectra recorded over a wavelength range of interest. In one embodiment, the optical signal data includes an intensity spectrum based on at least one pair of spectral lines from the calibrating light. The intensity spectrum can also be reduced to an integrated peak area ratio between a pair of spectral lines from the calibrating light. The integrated peak area ratio can be calculated using a spectrum of the calibrating light. In some embodiments, the intensity spectrum is a reference intensity spectra for the processing chamber and the spectrometer is further configured to determine an operational intensity spectrum for the plasma processing chamber 310.

The chamber controller 340 is configured to control the processing chamber 310 based on feedback from the spectrometer 330 or the local processing controller 360. As such, during a normal operation, such as a semiconductor etching or deposition process, the chamber controller 340 can adjust operation of the processing chamber 310 based on feedback from the spectrometer 330 or the local processing controller 360. The chamber controller 340 can also be used to adjust operating and configuration parameters of the processing chamber 310 for calibration of the processing chamber 310 based on the optical signal data generated by the spectrometer 330 or the local processing controller 360. The operating and configuration parameters include, gas pressure, gas mixture, temperature, RF power setting as well as the consideration of preventative maintenance operations and/or component repair/replacement. The spectrometer 330 and the local processing controller 360 may share any portion of the computational and spectral analysis of optical signal data as described herein. The local processing controller 360 may, for example, execute automated evaluation of the raw or calibrated optical signal data to determine unexpected variances and using rules, scripts, or even artificial intelligence to both determine what differences need attention and suggest chamber adjustments to better match the reference chamber.

FIG. 4A and FIG. 4B show multiple views of an embodiment of an optical calibrating device 400 suitable for placement into a plasma processing chamber, in accordance with an embodiment of the disclosure. The optical calibrating device 400 includes a main body 410 enclosing elements such as optical source 450, lamp trigger assembly 460 and logic circuitry 470. Optical source 450 can be a xenon flashlamp. Logic circuitry 470 can include lamp power control sub-systems, data and signal processors, flash counters, and memory for retaining optical signal data and other data such as discussed above with the memory 323 in FIG. 3.

The optical calibrating device 400 includes optical shaping elements, such as optic component baffles 480 and 482, and diffuser 484. Some of the optical shaping elements, such as optic component baffle 482 and diffuser 484, may be enclosed within an extension 420 of the optical calibrating device 400 which is connected with the main body 410. Diffuser 484 may be a diffusing plate such as the Edmund Optics Fused Silica Ground Glass diffuser #49237. More or less optical shaping elements may be included and the ordering of the components along the optical path may be varied to suit specific application of different embodiments of optical calibration devices. Diffuser 484 and baffles 480 and 482 operate together to form the broadband, continuous spectrum (e.g., from less than 200 nm in the UV to beyond 1100 nm in the infrared) of the source light from optical source 450 into a calibrating light that approximates plasma operating within a processing chamber and is less sensitive to orientation and placement within the processing chamber.

Light directing assembly 430 can be connected to or positioned within extension 420 and enclose further optical elements such as a turning mirror 435 that is positioned to direct the calibrating light to exit port 440. Light directing assembly 430 and optical shaping elements may be adapted to simulate different points of observation or positions within a processing chamber for example by the use of diffusers with differing homogenization angles, lens systems, etc.

The main body 410 and the extension 420 can define an enclosure that protects the various components of the optical calibration device 400. The enclosure can be made of a rigid material, such as a metal, to protect the optical calibration device 400. The enclosure can also include mounting hardware to secure the optical calibration device 400 within a processing chamber at specific predetermined locations appropriate for illuminating the optical viewport of a processing chamber.

The optical calibration device 400 can also include a rear panel assembly, interface panel 490, which includes features permitting control, powering and interaction with the optical calibration device 400. Interface panel 490 can include features such as power connectors, analog and digital signal connections, displays, control connectors for spectrometer synchronization, flash pulse counters, interlocks, etc. A text display 492 can also be used to indicate information such as number of flashes, calibration expiration warnings, lock-out conditions, error messages, etc. Communication to optical calibration device 400 may be bidirectional and transferred information may include raw or processed spectral data or other calibration data.

FIG. 5 shows a pictorial schematic 500 representing a configuration for orientating and mounting an optical calibration device 510 into a processing chamber 520, in accordance with an embodiment of the disclosure. The optical calibration device 510 may be mounted into processing chamber 520 at the appropriate location between wafer pedestal 530 and chamber lid 540. The orientation and location may be such that calibrating light 550 emitted from the optical calibration device 510 approximates emission from plasma during an operation in the processing chamber 520 and is projected through viewport 560 to components of an optical coupling system 570 and to spectrometer 580.

Optical calibration device 510 can be placed in the same location and angle relative to the viewport each time optical calibration device 510 is used. Changes in location (left-right, up-down, and angle) of optical calibration device 510 in the processing chamber 520 may affect the amplitude and spectral balance of the calibrating light entering the optical path, through the viewport 560 and the optical coupling system 570, to the spectrometer 580. The impact of these positional changes can also depend on the distance to the collection optics, i.e., the spectrometer 580, and the type of collection optics used. The optical calibration device 510 can include mounting hardware to precisely locate and securely fix the optical calibration device 510 to the processing chamber 520. The mounting hardware can be constructed to provide consistent positioning of the optical calibration device 510 within similar processing chambers to ensure that desired measurement accuracy and consistency is achieved. The combination of spectrometer, coupling optics, viewport conditions, chamber and calibration light source (at least) define the calibration state of any specific chamber. For each chamber the calibration state has different components (although of the same type or description) due to manufacturing variation. These are tracked to correctly identify the calibration state from chamber to chamber for matching purposes since the substitution of components may negate accurate calibration.

Figure 6:
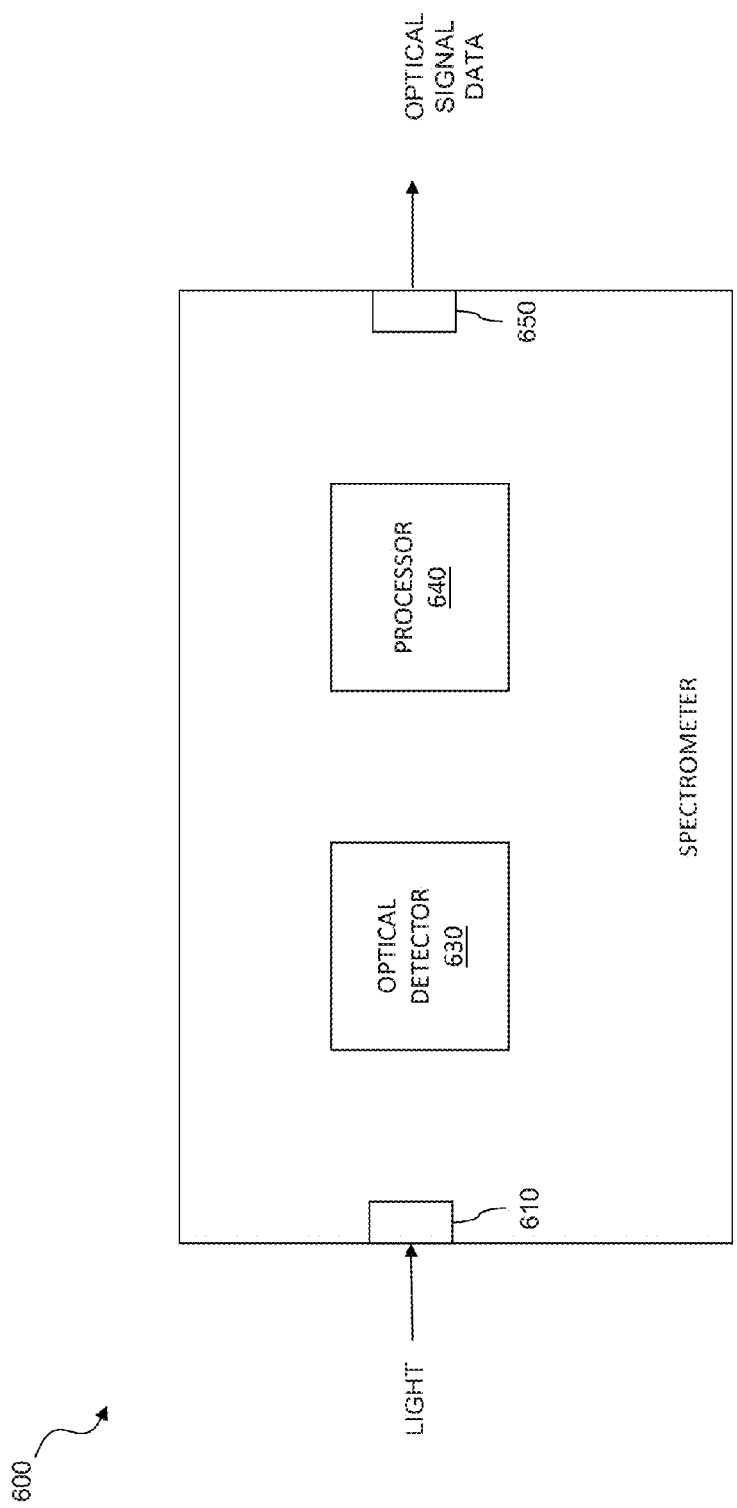
FIG. 6 is a block diagram of an embodiment of a spectrometer constructed according to the principles of the disclosure.

FIG. 6 illustrates a block diagram of an embodiment of a spectrometer 600 constructed according to the principles of the disclosure. The spectrometer 600 is configured to make optical measurements and includes at least three functionally separate components: a light dispersing component for dispersing light into a spectrum, an optical detector for converting the spectral light into raw spectral intensity data and processing capability, software and/or firmware for converting the raw spectral intensity data into optical signal data. The spectrometer 600 includes an optical detector 630 and a processor 640. The spectrometer 600 can include additional components that a conventional spectrometer includes, such as a display for communicating with a user.

The optical detector 630 is an optical component that converts spectral light into raw spectral intensity data. The optical detector 630 is configured to receive light via an input port 610 coupled to an optical coupling system such as illustrated in FIG. 1.

The processor 640 is configured to convert the raw spectral intensity data into optical signal data that can be provided to a subsequent system or operator via an output port 650. The processor 640 is also configured to determine optical signal data from the raw spectral intensity data. The optical signal data can be raw uncalibrated intensity data or processed intensity data (or any portion thereof). In one embodiment, the optical signal data is an intensity ratio for two spectral lines of the raw spectral intensity data. In one embodiment, the processor 640 determines the intensity ratio by comparing the areas under the wavelength peaks (i.e., peak areas) for selected wavelengths. In some embodiments, the peak areas are determined from the data of the processor 640. The selected spectral data can be generated from a light source, such as from the optical calibrating device 320, 400, or 510, to provide a reference intensity ratio, or from the plasma of a processing chamber to provide an operational intensity ratio. In some embodiments, the processor 640 is also configured to determine a characterization ratio for a pair of processing chambers based on the determined intensity ratios from the selected wavelengths. In other embodiments, another processing system device, such as a local processing controller, tool controller, or a master process controller, is configured to receive monitoring data from the spectrometer 600 and based thereon determine the characterization ratio. In some embodiments, the other devices can also be configured to determine the respective optical signal data from monitoring data received via the spectrometer 600. Detailed examples of optical signal data collection, processing and analysis are described in association with the methods described herein below. In alternative embodiments, processing described above may be complete whole or in part by a system, computing device, processor, etc., that is external to, e.g., a different device, the spectrometer 600, such as by the local processing controller 360 of FIG. 3.

Figure 7:
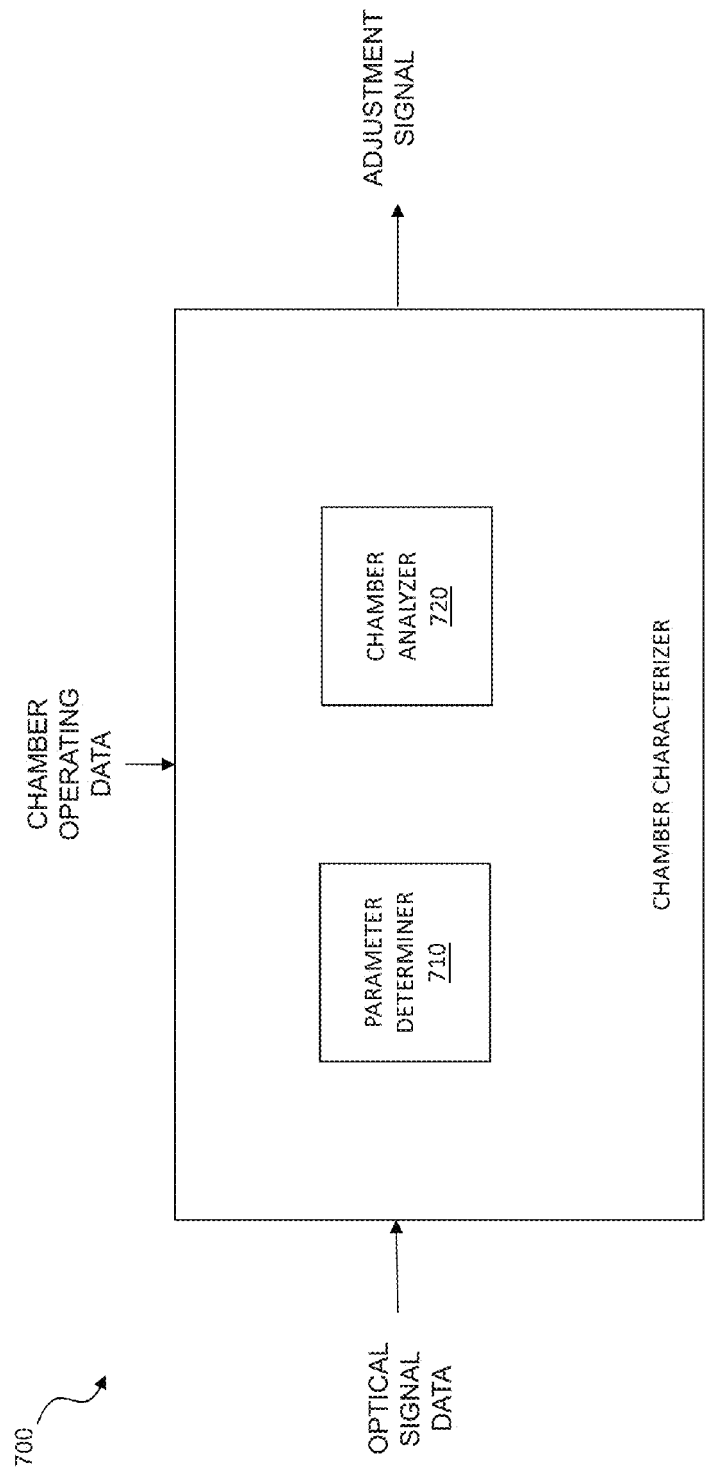
FIG. 7 is a block diagram of an embodiment of a chamber characterizer for a processing chamber constructed according to the principles of the disclosure.

FIG. 7 illustrates a block diagram of an embodiment of a chamber characterizer 700 for plasma processing chambers constructed according to the principles of the disclosure. The chamber characterizer 700 is configured to provide a chamber adjustment signal to be used to obtain uniform processing between plasma processing chambers. The functionality of the various components of the chamber characterizer 700 can be integral to a single computing device or can be distributed among multiple computing devices. The chamber characterizer 700 or portions of the functionality of the chamber characterizer 700, can be integrated within a spectrometer, a local processing controller, a tool controller, a line controller, or a designated computing device, or distributed in a combination thereof. The chamber characterizer 700 includes a parameter determiner 710 and a chamber analyzer 720.

The parameter determiner 710 is configured to receive spectral data and determine therefrom various parameters, such as matching parameters, and associated values that are useful for control and matching of process chambers. In a specific example to characterize and match plasma temperature, the parameter determiner 710 is configured to determine intensity ratios of specific spectra lines associated with processing chambers and, based thereon, determine a characterization ratio representative of the state of the plasma temperature. In one embodiment, the parameter determiner 710 calculates a reference intensity ratio between two selected wavelengths for a reference chamber (R1L) and also calculates an operational intensity ratio between the two selected wavelengths for the reference chamber (R1C). Similarly, the parameter determiner 710 calculates the reference intensity ratio (R2L) between the same two selected wavelengths for a second chamber and the operational intensity ratio (R2C) between the same two selected wavelengths for the second chamber. The parameter determiner 710 is further configured to determine the characterization ratio for the two chambers based on the intensity ratios (R21=R2C/R1C×R1L/R2L). In one embodiment, the parameter determiner 710 receives spectral intensity data from a spectrometer, such as spectrometer 600, to calculate these ratios. Although the specific operational and reference intensity ratios in the above described example are defined using specific wavelength regions, these ratios may also include any portion of available optical signal data such as discussed in association with calibration curves 1055, 1060, 1065 and 1070 of FIG. 10B. Additionally, the characterization ratio as described above uses a specific mathematical combination of the intensity ratios and it should be understood that different combinations of various portions of the intensity ratios and other optical signal data may be combined to produce a different characterization ratio in support of a chamber matching metric differing from plasma temperature.

The chamber analyzer 720 is configured to provide a chamber adjustment signal based on the characterization ratio received from the parameter determiner 710. The chamber analyzer 720 also receives chamber operating data that is used to determine the chamber adjustment signal. The chamber adjustment signal is used to tune the second chamber to maintain the characterization ratio or other identified parameter to achieve uniform processing between the reference chamber and second chamber. Chamber analyzer 720 may work cooperatively with an associated spectrometer and chamber controller via a neutral net, PID control or other method to adjust chamber operational parameters to achieve a designed result such as a characterization ratio approaching unity which indicates (based upon this parameterization) matched chambers. An adjustment signal may be broadly defined to be a process control parameter such as RF power setting or may be an indication of needed repair or replacement of a system component that is affecting process conditions and matching.

Figure 8:
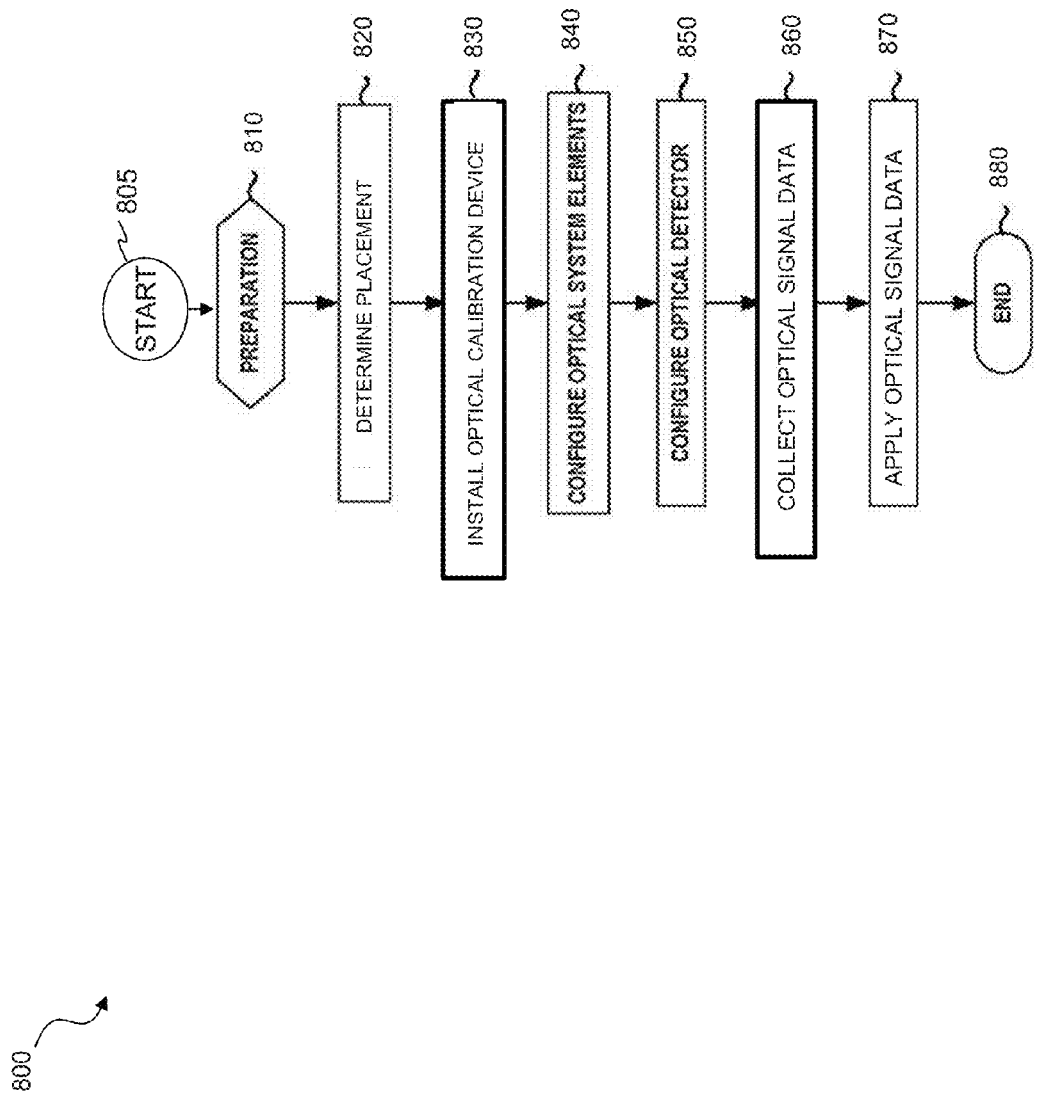
FIG. 8 is a flow chart of an embodiment of a method for orientating, mounting and operating an optical calibration device in a processing chamber, carried out according to the principles of the disclosure.

FIG. 8 shows a flow chart for an embodiment of a method 800 for orientating, mounting and operating an optical calibration device into a plasma processing chamber in accordance with the disclosure. The processing chamber can be coupled to an optical system for monitoring and calibrating. The method 800 can be used with a single processing chamber, such as one of the processing chambers of FIG. 1, for calibration of the optical system associated with that processing chamber. Additionally, the method 800 can be used with all of the processing chambers of FIG. 1 for chamber to chamber calibration. The method 800 begins in step 805.

The method 800 continues with a preparation step 810 wherein any preliminary setup and configuration of the optical calibration device may be performed. Preparatory actions can include, for example, "burning-in" an optical source, such as a flashlamp, to mitigate the potential for short-term optical signal drift and/or variation due to lamp drift. Next in step 820, placement or positioning of the optical calibration device into a plasma processing chamber is determined. Placement can be proximate a viewport of the processing chamber and permit calibrating light emitted from the optical calibration device to subtend space and angles at the viewport approximating an observed plasma. The placement of the optical calibration device within the processing chamber may be predetermined based on location space options and mounting hardware. Next in step 830, the optical calibration device is installed within the plasma processing chamber. For repeatable calibration, the optical calibration device can be securely mounted with constant position and orientation from installation to installation over multiple processing chambers for which calibration and matching is desired. As noted above, mounting hardware can be used for the repeatable positioning.

In step 840, configuration of the optical system components may be performed. Configuration may include, for example, properly installing, cleaning and connecting viewports, optical filters, lenses and optical fibers. It should be noted that calibration may be negatively impacted or erroneous if the optical system components are inconsistently configured between calibration and actual use. Subsequently in step 850, an optical detector, such as a spectrometer, may be configured for use with the optical calibration device. In one embodiment, a spectrometer may be configured to trigger the optical source of the optical calibration device at specific intensity levels at specific rates for a defined duration or number of flashes of the optical source.

In multiple embodiments, the spectrometer interacting with the optical source of the optical calibration device is advantageously the same spectrometer that normally monitors the plasma emission from the processing chamber. Using a different spectrometer may add complexity to the method used by chamber characterizer 700. The spectrometer may also query from the optical calibration device optical signal data, processing control information, and other information and use responses to queries to support the calibration process. Once any configuration is complete, method 800 advances to step 860 where optical signal data may be collected. Optical signal data may be optical spectral collected by the spectrometer for a specific number of flashes, e.g., 100, of the optical source while the optical source is operated under conditions required to avoid saturating conditions as well as producing signals of sufficient amplitude at any desired wavelengths. The collection of optical signal data may also take place in the presence of ambient light and under these conditions optical signal measurements may be made as a difference measurement (flash-on minus flash-off).

In step 870, measured optical signal data may be combined with reference optical signal data to determine corrections for each calibrated system. One goal of calibration is to use the measured intensity optical signal data as part of a correction vector for scaling/offsetting the optical signal intensities as recorded by any spectrometer. In general, a reference spectrum, either associated with the optical calibration device or with a "reference chamber" can be used to calculate a ratio of the reference spectrum to the measured spectrum which may be applied within hardware or software, enabling the correction of real time data useful for real-time wafer processing or chamber matching. A factory measured spectrum, associated with a specific optical calibration device, may be collected prior to use of the optical calibration device and stored therein. In some embodiments, a tool controller or a processor of the spectrometer may be configured to determine the ratio. Another computing device can also be used. Method 800 ends in a step 880.

FIG. 9 illustrates a flow diagram of an embodiment of a method 900 of characterizing and matching process chambers carried out according to the principles of the disclosure. The method 900 can be used, for example, to match multiple processing chambers within a tool, corresponding processing chambers in different tools, all the processing chambers within a tool or multiple tools, calibration of a single chamber, and other chamber matching combinations depending on the needed application. Method 900 starts with a step 905. In step 910, a plasma is generated in a process chamber that may be a "reference" chamber which is operating as specifically desired to achieve a known result. In step 920, spectra may be recorded by a spectrometer associated with the chamber of step 910. In step 930, a standardized light source, such as provided by an optical calibration device as disclosed herein, is placed in the same chamber and in step 940 additional spectra is recorded. The spectra from step 920 may be considered operational spectra and the spectra from step 940 may be considered calibration spectra as discussed herein. In step 950, plasma spectra may be calibrated using a calibration spectrum from the light source and calibration values may be determined for the chamber. Calibration of spectra may be supported by transfer of information to/from the light source such as a factory measured calibration spectrum associated with a specific light source serial number to a spectrometer. Process 900 may terminate at this step if no chamber matching is to be done. In this case, the calibration data can be stored in memory associated with the light source (such as a memory of an optical calibration device), into the spectrometer or to another location such as a chamber controller and used to calibrate future operational spectra for this chamber.

In step 960 calibrated spectra may be analyzed for adjustment or matching parameters for the desired observable (temperature, pressure, density, etch rate, etc.). In step 970 comparison may be done between adjustment/matching parameters of comparable chambers. In step 980 the operating conditions of a chamber may be modified based upon differences in determined adjustment/matching parameters. Process 900 ends with step 990.

Figure 10A:
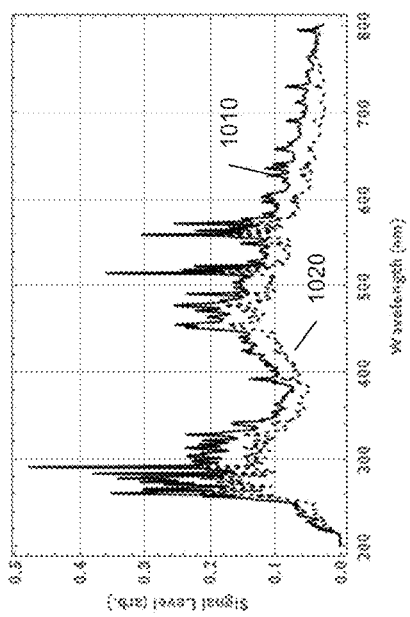
FIGS. 10A, 10B, and 10C show a set of plots indicating optical signal data collected and processed in association with the method of FIG. 9.
Figure 10B:
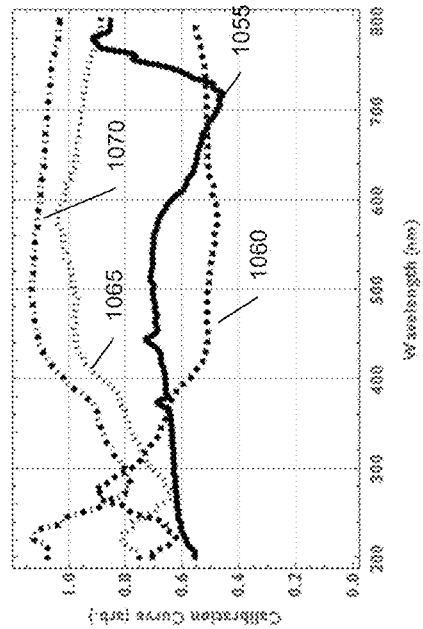
Figure 10C:
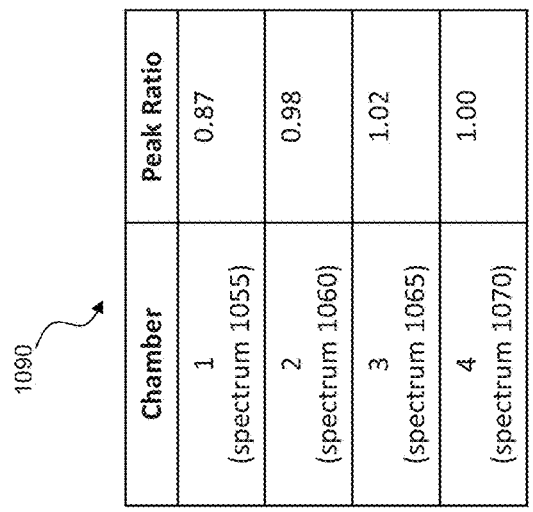

FIGS. 10A, 10B, and 10C show a set of plots indicating optical signal data collected and processed in association with the method of FIG. 9, according to the principles of the disclosure. Plot 1000 of FIG. 10A shows two spectra 1010 and 1020 that indicate, respectively, a factory-measured light source spectra and a measured spectra from the light source placed within a chamber. Factory-measured calibration spectrum 1010 may be stored internal to an optical calibration device for recall by an associated spectrometer that is recording spectra. Measured spectrum 1020 differs from spectrum 1010 and the differences are determined by a ratio calculation and resultant calibration curve 1055 of plot 1050 in FIG. 10B. Spectrum 1020 indicates attenuation across all portions of the wavelength range and may, for example, be due to contamination of a viewport or damage/wear to another optical component and lack of spectrometer calibration.

Additional calibration curves 1060, 1065, and 1070 are shown in plot 1050 of FIG. 10B. Each calibration curve may be associated with a specific combination of chamber, calibration light source, spectrometer and intervening optics that define the overall measured "system." In the case where the same spectrometer and light source were used for collection (or where additional normalization to remove the spectrometer and/or light sources scaling has been accommodated) of the spectra of plot 1050, the differences in the calibration curves may indicate changes in the optical system components between the light source and the spectrometer. For example, when spectra 1065 and 1070 are compared overall shape is similar but the relative amplitude is approximately 20% different. This change may indicate that an optical aperture within the chamber is becoming restricted in the chamber associated with spectrum 1065. It should be noted that the discussion associated with FIGS. 10A-10C is specific to calibration or reference spectral data and not to operational spectral data from a plasma process. Overall chamber matching and comparison may be divided into two processes which permit separation of calibration or reference analysis and operational analysis. Calibration analysis may be performed firstly and may be advantageously used to determine hardware differences or problems for single chambers or between chambers. Operational analysis of actual measured plasma light may be used subsequently to more specifically determine operational conditions or differences of or among chambers.

Differences may be evaluated manually and by automated algorithms executing on the chamber controller, tool controller, and/or another connected computer such as the local processing controller. Automated evaluation of the optical signal data advantageously permits more consistent and procedural adjustments to eliminate guesswork and minimize variation versus making manual adjustments across chambers and between operators. Automated evaluation should yield specific adjustment instructions for either the operator or chamber controller so manual or automated adjustments can be made optimally.

Figure 11:
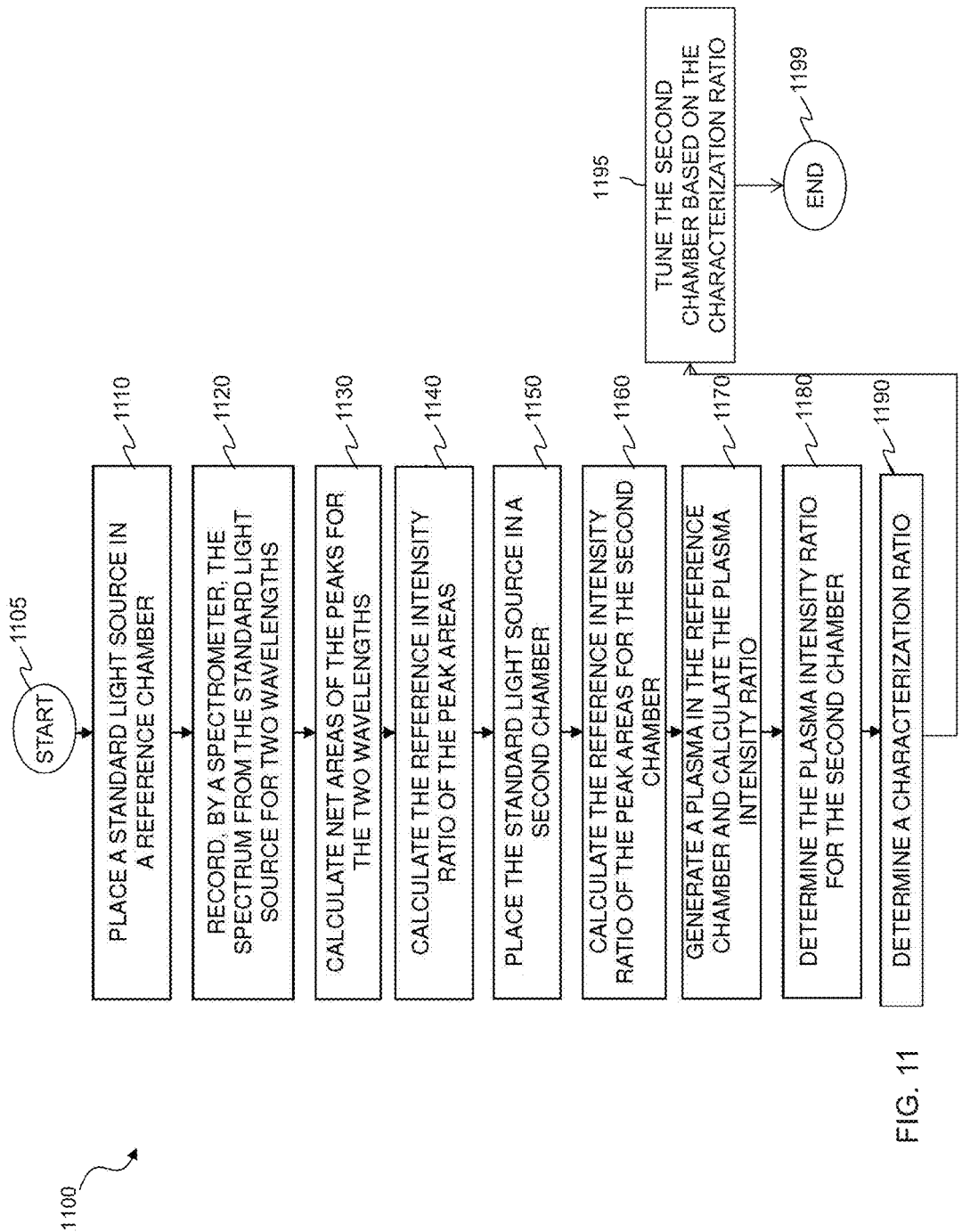
FIG. 11 is a flow chart of an embodiment of a method of characterizing and matching process chambers using predetermined spectral features carried out according to the principles of the disclosure.

As discussed further in the specific example of FIG. 11, table 1090 in FIG. 10C summarizes a list of peak ratio values which would result if calibration was not applied to recorded data. Table 1090 includes a chamber column and an associated peak ratio column. The chamber column includes a spectrum from four different chambers and the peak ratio column includes the corresponding peak ratios. FIG. 11 illustrates a flow diagram of an embodiment of a method 1100 of characterizing and matching process chambers carried out according to the principles of the disclosure. The method 1100 begins in a step 1105.

In a step 1110, a standard light source is placed in a reference chamber. The standard light source can be an optical calibration device. In one embodiment, the standard light source is placed to approximate the location from which the plasma light will be generated in the chamber. The light will pass through the viewport window of the reference processing chamber and any collection optics, and into the fiber optic on the optimal chamber of a spectrometer.

In a step 1120, one or more spectra from the standard light source are recorded by the spectrometer. For a parameter based upon line ratios, the spectrum from the standard light source for at least two wavelengths are recorded by the spectrometer. Calculations may be performed in step 1130 to determine processing methods for parameter determination. In a specific example, net areas of the peaks for the two wavelengths as recorded by the spectrometer are calculated in a step 1130. In one embodiment, corrections for any background and light from other sources beside the standard light source are made.

The reference intensity ratio R1L of the peak areas for the pair of lines is calculated in a step 1140. In a step 1150, the standard light source is placed in a second chamber, in the manner described above in step 1110. The reference intensity ratio R2L is determined in a step 1160. The same process as described above to calculate R1L is used to calculate R2L.

A plasma is then generated in the reference chamber in a step 1170. The plasma intensity ratio for the reference chamber R1C is then calculated based on the net areas of the peaks of the recorded spectrum as discussed above. In a step 1180, the plasma intensity ratio for the second chamber R2C is then determined according to the same process used to determine R1C. In a step 1190, a characterization ratio R21 is determined based on the reference intensity ratios and the plasma intensity ratios. In a step 1195, the second chamber is tuned until the characterization ratio R21 is as close as possible to one. A tool controller may be used to adjust the energy level of the plasma of the second chamber to maintain a characterization ratio of one. The method 1100 ends in a step 1199.

The disclosure recognizes the ability to perform "chamber-matching" and to observe known relative or identical optical emission changes/conditions amongst multiple chambers can be used to permit uniform usage of processing chambers as well as understand performance differences thereof. Matching parameters can be determined and used for the chamber matching.

Calibration may be performed in a variety of ways that result in "standardized" signals. For example in the case of a single calibration light source used with multiple chambers, each with an associated spectrometer, calibration may result in individual correction vectors each associated with each chamber/spectrometer pair. In this example the overall observed signals may or may not be "referenced" to a defined standard signal for chamber. In the case of multiple calibration light sources, each light source may be associated with a pre-determined set of calibration data (spectral signal of wavelength) which permits determination of relative corrections, pertaining to light source differences, to be accommodated. Association of any observed or corrected signal level may ultimately be associated with a defined "standard", such as a NIST traceable reference source but this is not required.

The changes described above, and others, may be made in the optical measurement systems and subsystems described herein without departing from the scope hereof. For example, although certain examples are described in association with semiconductor wafer processing equipment, it may be understood that the optical measurement systems described herein may be adapted to other types of processing equipment such as roll-to-roll thin film processing, solar cell fabrication, flat panel display processing, or any application where high precision optical measurement may be required. Furthermore, although certain embodiments discussed herein describe the use of a common light analyzing device, such as an imaging spectrograph; it should be understood that multiple light analyzing devices with known relative sensitivity may be utilized. Furthermore, although the term "wafer" has been used herein when describing aspects of the current disclosure; it should be understood that other types of workpieces such as quartz plates, phase shift masks, LED substrates and other non-semiconductor processing related substrates and workpieces including solid, gaseous and liquid workpieces may be used.

The embodiments described herein were selected and described in order to best explain the principles of the disclosure and the practical application, and to enable others of ordinary skill in the art to understand the disclosure for various embodiments with various modifications as are suited to the particular use contemplated. The particular embodiments described herein are in no way intended to limit the scope of the present disclosure as it may be practiced in a variety of variations and environments without departing from the scope and intent of the disclosure. Thus, the present disclosure is not intended to be limited to the embodiment shown, but is to be accorded the widest scope consistent with the principles and features described herein.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As will be appreciated by one of skill in the art, the disclosure may be embodied as a method, system, or computer program product. Accordingly, the features disclosed herein, or at least some of the features, may take the form of an entirely hardware embodiment, an entirely software embodiment (including firmware, resident software, microcode, etc.) or an embodiment combining software and hardware aspects all generally referred to herein as a "circuit" or "module." Furthermore, features or at least some of the features disclosed herein may take the form of a computer program product on a non-transitory computer-usable storage medium having computer-usable program code embodied in the medium.

Thus, portions of disclosed examples may relate to computer storage products with a non-transitory computer-readable medium that have program code thereon for performing various computer-implemented operations that embody a part of an apparatus, device or carry out the steps of a method set forth herein. Non-transitory used herein refers to all computer-readable media except for transitory, propagating signals. Examples of non-transitory computer-readable media include, but are not limited to: magnetic media such as hard disks, floppy disks, and magnetic tape; optical media such as CD-ROM disks; magneto-optical media such as floptical disks; and hardware devices that are specially configured to store and execute program code, such as ROM and RAM devices. Examples of program code include both machine code, such as produced by a compiler, and files containing higher level code that may be executed by the computer using an interpreter.

A portion of the above-described apparatus, systems or methods may be embodied in or performed by various, such as conventional, digital data processors or computers, wherein the computers are programmed or store executable programs of sequences of software instructions to perform one or more of the steps of the methods. The software instructions of such programs may represent algorithms and be encoded in machine-executable form on non-transitory digital data storage media, e.g., magnetic or optical disks, random-access memory (RAM), magnetic hard disks, flash memories, and/or read-only memory (ROM), to enable various types of digital data processors or computers to perform one, multiple or all of the steps of one or more of the above-described methods, or functions, systems or apparatuses described herein.

Various aspects of the disclosure can be claimed including the systems and methods as disclosed herein.

Aspects disclosed herein include:

A. An optical calibration device including: (1) an enclosure, (2) an optical source located within the enclosure and configured to provide a source light having a continuous spectrum, and (3) optical shaping elements located within the enclosure and configured to form the source light into a calibrating light that approximates a plasma emission during an operation within the processing chamber.

B. A characterization system including: (1) an optical calibration device positioned within a plasma processing chamber having a viewport, (2) an optical coupling system coupled to the viewport and positioned to receive calibrating light emitted by the optical calibration device, and (3) a spectrometer optically coupled to the optical calibration device via the optical coupling system and configured to generate and report measured optical signal data associated with the calibrating light and propagation of the calibrating light through the plasma processing chamber, the viewport, and the optical coupling system.

C. A method of characterizing plasma processing chambers including: (1) positioning an optical calibration device within a plasma processing chamber having a viewport, (2) coupling an optical coupling system to the viewport, the optical coupling system positioned to receive calibrating light emitted by the optical calibration device, (3) coupling an optical detector to the optical calibration device via the optical coupling system, and (4) configuring the optical detector to generate and report measured optical signal data associated with the calibrating light and its propagation through the plasma processing chamber, the viewport and the optical coupling system.

D. A method of characterizing plasma processing chambers including: (1) determining a first reference intensity ratio and a first operational intensity ratio of a reference plasma processing chamber, (2) determining a second reference intensity ratio and a second operational intensity ratio of a second plasma processing chamber, and (3) determining a characterization ratio of emitted light from the reference and second plasma chambers using a mathematical combination of the first and second reference intensity ratios and the first and second operational intensity ratios.

E. A chamber characterizer includes a non-transitory computer readable medium having a series of instructions stored thereon that when executed cause a processor to: (1) determine a first reference intensity ratio and a first operational intensity ratio of a reference plasma processing chamber, (2) determine a second reference intensity ratio and a second operational intensity ratio of a second plasma processing chamber, and (3) determine a characterization ratio of emitted light from the reference and second plasma chambers based on a mathematical combination of the first and second reference intensity ratios and the first and second operational intensity ratios.

Each of aspects A, B, C, D, and E may have one or more of the following additional elements in combination: Element 1: wherein the optical shaping elements are selected from the group consisting of diffusers, baffles, lenses, mirrors, apertures, filters, and windows. Element 2: wherein the optical source is a xenon flashlamp. Element 3: logic circuitry located within the enclosure that is configured to control operation of the optical source and to communicate with an external system. Element 4: wherein the calibrating light has a wavelength range, spatial extent and angular extent at least equal to that provided the plasma emission and observed by an optical detector. Element 5: wherein the optical source is a flashlamp and the optical calibration device further includes a trigger assembly, coupled to the logic circuitry and the optical source, configured to provide triggering signals to the flashlamp. Element 6: wherein the triggering signals include alternating flash-on and flash-off signals. Element 7: wherein the enclosure includes a main body and an extended body, wherein at least a portion of the optical shaping elements are located within the extended body. Element 8: wherein the operation is a semiconductor wafer process. Element 9: wherein the optical signal data includes an intensity ratio based on a portion of two or more spectra from the measured optical signal data. Element 10: wherein the spectrometer is further configured to generate and report measured optical signal data associated with plasma light and propagation of the plasma light through the plasma processing chamber, the viewport, and the optical coupling system. Element 11: wherein the optical coupling system includes a fiber optical cable, and the spectrometer includes an optical port for receiving the calibrating light via the fiber optical cable. Element 12: wherein the optical calibration device includes an enclosure, an optical source located within the enclosure and configured to provide a source light having a continuous spectrum, and optical shaping elements located within the enclosure and configured to form the source light into the calibrating light that approximates a plasma emission during an operation within the plasma processing chamber. Element 13: wherein the optical calibration device further includes logic circuitry located within the enclosure that is configured to control operation of the optical source and to communicate with an external system. Element 14: wherein the optical source is a flashlamp and the optical calibration device further includes a trigger assembly, coupled to the logic circuitry and the optic source, configured to provide triggering signals to the flashlamp. Element 15: wherein the logic circuitry further comprises a memory storing a reference spectrum for the optical calibration device. Element 16: further comprising configuring the optical detector to generate and report measured optical signal data associated with plasma light and propagation of the plasma light through the plasma processing chamber, the viewport, and the optical coupling system. Element 17: further comprising placing an optical calibration device in the reference plasma processing chamber and in the second plasma processing chamber, and generating a calibrating light from the optical calibration device in each of the reference and the second plasma processing chambers. Element 18: wherein the determining the first reference intensity ratio includes recording at least one spectrum from the calibrating light in the reference plasma processing chamber and calculating a matching parameter based on optical signal data. Element 19: wherein the determining the first operational intensity ratio includes generating a plasma in the reference plasma processing chamber and recording at least one spectrum from light emitted from the plasma in the reference plasma processing chamber and calculating a matching parameter based on optical signal data. Element 20: further comprising tuning the second plasma processing chamber using the characterization ratio. Element 21: wherein to determine the first reference intensity ratio, the processor is configured to execute the instructions to record at least one spectrum from a calibrating light in the reference plasma processing chamber and calculate a matching parameter. Element 22: wherein to determine the reference operational intensity ratio, the processor is configured to execute the instructions to record at least one spectrum from a plasma in the reference plasma processing chamber and calculate a matching parameter. Element 23: wherein the processor is configured to execute the instructions to provide a chamber adjustment signal using the characterization ratio to tune the second plasma chamber for uniform processing between the reference plasma chamber and the second plasma chamber.

What is claimed is:

1. An optical calibration device for in-chamber calibration of optical signals associated with a processing chamber, comprising:
   an enclosure;
   an optical source located within the enclosure and configured to provide a source light having a continuous spectrum; and optical shaping elements located within the enclosure and configured to form the source light into a calibrating light that approximates a plasma emission during an operation within the processing chamber, the calibrating light having a wavelength range, spatial extent and angular extent at least equal to that provided by the plasma emission and observed by an optical detector coupled to the plasma chamber via an optical coupling system.

2. The optical calibration device as recited in claim 1 wherein the optical shaping elements are selected from the group consisting of diffusers, baffles, lenses, mirrors, apertures, filters, and windows.

3. The optical calibration device as recited in claim 1 wherein the optical source is a xenon flashlamp.

4. The optical calibration device as recited in claim 1 further comprising logic circuitry located within the enclosure that is configured to control operation of the optical source and to communicate with an external system.

5. The optical calibration device as recited in claim 4 wherein the optical source is a flashlamp and the optical calibration device further includes a trigger assembly, coupled to the logic circuitry and the optical source, configured to provide triggering signals to the flashlamp.

6. The optical calibration device as recited in claim 5 wherein the triggering signals include alternating flash-on and flash-off signals.

7. The optical calibration device as recited in claim 1 wherein the enclosure includes a main body and an extended body, wherein at least a portion of the optical shaping elements are located within the extended body.

8. The optical calibration device as recited in claim 1 wherein the operation is a semiconductor wafer process.

9. A characterization system for plasma processing chambers, comprising:
an optical calibration device positioned within a plasma processing chamber having a viewport;
an optical coupling system coupled to the viewport and positioned to receive calibrating light emitted by the optical calibration device, the calibrating light approximating a plasma emission during an operation within the plasma processing chamber; and
a spectrometer optically coupled to the optical calibration device via the optical coupling system and configured to generate and report measured optical signal data associated with the calibrating light and propagation of the calibrating light through the plasma processing chamber, the viewport, and the optical coupling system, the calibrating light having a wavelength range, spatial extent and angular extent at least equal to that provided by the plasma emission and observed by the spectrometer.

10. The characterization system as recited in claim 9 wherein the optical signal data includes an intensity ratio based on a portion of two or more spectra from the measured optical signal data.

11. The characterization system as recited in claim 9 wherein the spectrometer is further configured to generate and report measured optical signal data associated with plasma light and propagation of the plasma light through the plasma processing chamber, the viewport, and the optical coupling system.

12. The characterization system as recited in claim 9 wherein the optical coupling system includes a fiber optical cable, and the spectrometer includes an optical port for receiving the calibrating light via the fiber optical cable.

13. The characterization system as recited in claim 9 wherein the optical calibration device includes:
an enclosure;
an optical source located within the enclosure and configured to provide a source light having a continuous spectrum; and
optical shaping elements located within the enclosure and configured to form the source light into the calibrating light that approximates the plasma emission.

14. The characterization system as recited in claim 13 wherein the optical source is a xenon flashlamp.

15. The characterization system as recited in claim 13 wherein the optical shaping elements are selected from the group consisting of diffusers, baffles, lenses, mirrors, apertures, filters, and windows.

16. The characterization system as recited in claim 13 wherein the optical calibration device further includes logic circuitry located within the enclosure that is configured to control operation of the optical source and to communicate with an external system.

17. The characterization system as recited in claim 16 wherein the optical source is a flashlamp and the optical calibration device further includes a trigger assembly, coupled to the logic circuitry and the optic source, configured to provide triggering signals to the flashlamp.

18. The characterization system as recited in claim 16 wherein the logic circuitry further comprises a memory storing a reference spectrum for the optical calibration device.

19. A method of characterizing plasma processing chambers, comprising:
positioning an optical calibration device within a plasma processing chamber having a viewport;
coupling an optical coupling system to the viewport, the optical coupling system positioned to receive calibrating light emitted by the optical calibration device, the calibrating light approximating a plasma emission during an operation within the plasma processing chamber;
coupling an optical detector to the optical calibration device via the optical coupling system; and
configuring the optical detector to generate and report measured optical signal data associated with the calibrating light and its propagation through the plasma processing chamber, the viewport and the optical coupling system, wherein the calibrating light has a wavelength range, spatial extent, and angular extent at least equal to that provided by the plasma emission and observed by the optical detector.

20. The method of characterization as recited in claim 19 further comprising configuring the optical detector to generate and report measured optical signal data associated with plasma light and propagation of the plasma light through the plasma processing chamber, the viewport, and the optical coupling system.

21. A method of characterizing plasma processing chambers, comprising:
placing an optical calibration device in a reference plasma processing chamber and in a second plasma processing chamber;
generating a calibrating light from the optical calibration device in each of the reference and the second plasma processing chambers, the calibrating light having a wavelength range, spatial extent and angular extent at least equal to that provided by a plasma emission during an operation within the reference plasma processing chamber or the second plasma processing chamber and observed by an optical detector coupled to the reference plasma processing chamber or the second plasma processing chamber via an optical coupling system;

determining a first reference intensity ratio and a first operational intensity ratio of the reference plasma processing chamber;

determining a second reference intensity ratio and a second operational intensity ratio of the second plasma processing chamber; and determining a characterization ratio of emitted light from the reference and second plasma processing chambers using a mathematical combination of the first and second reference intensity ratios and the first and second operational intensity ratios.

22. The method as recited in claim 21 wherein the determining the first reference intensity ratio includes recording at least one spectrum from the calibrating light in the reference plasma processing chamber and calculating a matching parameter based on optical signal data.

23. The method as recited in claim 21 wherein the determining the first operational intensity ratio includes generating a plasma in the reference plasma processing chamber and recording at least one spectrum from light emitted from the plasma in the reference plasma processing chamber and calculating a matching parameter based on optical signal data.

24. The method as recited in claim 21 further comprising tuning the second plasma processing chamber using the characterization ratio.

25. A chamber characterizer, comprising:
a non-transitory computer readable medium having a series of instructions stored thereon that when executed cause a processor to:
record at least one spectrum from a calibrating light in a reference plasma processing chamber, the calibrating light having a wavelength range, spatial extent and angular extent at least equal to that provided by a plasma emission during an operation within the reference plasma processing chamber and observed by an optical detector coupled to the reference plasma processing chamber via an optical coupling system;
calculate a matching parameter employing the at least one spectrum from the calibrating light;
determine a first reference intensity ratio employing the matching parameter and determine a first operational intensity ratio of a reference plasma processing chamber;
determine a second reference intensity ratio and a second operational intensity ratio of a second plasma processing chamber; and
determine a characterization ratio of emitted light from the reference and second plasma chambers based on a mathematical combination of the first and second reference intensity ratios and the first and second operational intensity ratios.

26. The chamber characterizer as recited in claim 25 wherein to determine the reference operational intensity ratio, the processor is configured to execute the instructions to record at least one spectrum from a plasma in the reference plasma processing chamber and calculate a matching parameter employing the at least one spectrum from the plasma.

27. The chamber characterizer as recited in claim 25 wherein the processor is configured to execute the instructions to provide a chamber adjustment signal using the characterization ratio to tune the second plasma chamber for uniform processing between the reference plasma chamber and the second plasma chamber.

\* \* \* \* \*